United States Patent
Yoo et al.

(10) Patent No.: US 12,295,753 B2
(45) Date of Patent: *May 13, 2025

(54) METHOD AND SYSTEM FOR DETERMINING ABNORMALITY IN MEDICAL DEVICE

(71) Applicant: LUNIT INC., Seoul (KR)

(72) Inventors: Donggeun Yoo, Seoul (KR); Sanghyup Lee, Seoul (KR); Minchul Kim, Seoul (KR); Hanjun Lee, Seoul (KR); Sunggyun Park, Seoul (KR)

(73) Assignee: LUNIT INC., Seoul (KR)

(*) Notice: Subject to any disclaimer, the term of this patent is extended or adjusted under 35 U.S.C. 154(b) by 217 days.

This patent is subject to a terminal disclaimer.

(21) Appl. No.: 17/973,672

(22) Filed: Oct. 26, 2022

(65) Prior Publication Data
US 2023/0053280 A1     Feb. 16, 2023

Related U.S. Application Data

(63) Continuation of application No. PCT/KR2021/006163, filed on May 17, 2021.

(30) Foreign Application Priority Data

May 18, 2020 (KR) .................. 10-2020-0059347
May 17, 2021 (KR) .................. 10-2021-0063464

(51) Int. Cl.
*A61B 6/00* (2024.01)
*A61B 5/00* (2006.01)
*G06T 7/00* (2017.01)

(52) U.S. Cl.
CPC .......... *A61B 5/7264* (2013.01); *A61B 6/5217* (2013.01); *G06T 7/0012* (2013.01)

(58) Field of Classification Search
CPC ... A61B 5/7264; A61B 6/5217; A61B 5/0033; A61B 6/025; A61B 6/032; A61B 6/037;
(Continued)

(56) References Cited

U.S. PATENT DOCUMENTS

2003/0220557 A1   11/2003   Cleary et al.
2010/0217116 A1    8/2010   Eck et al.
(Continued)

FOREIGN PATENT DOCUMENTS

JP     2009519083 A      5/2009
JP     2019524284 A      9/2019
KR   1020190130310 A    11/2019

OTHER PUBLICATIONS

Xin Yi, Scott J. Adams, Robert D. E. Henderson, and Paul Babyn: "Computer-aided Assessment of Catheters and Tubes on Radiographs: How Good Is Artificial Intelligence for Assessment?", Jan. 29, 2020, Radiology: Artificial Intelligence 2020, pp. 1-9. (Year: 2020).*

(Continued)

*Primary Examiner* — Siamak Harandi
(74) *Attorney, Agent, or Firm* — Sughrue Mion, PLLC

(57) ABSTRACT

A method for determining an abnormality in a medical device from a medical image is provided. The method for determining an abnormality in a medical device comprises receiving a medical image, and detecting information on at least a part of a target medical device included in the received medical image.

20 Claims, 14 Drawing Sheets

(58) Field of Classification Search
CPC ....... A61B 6/468; A61B 6/502; A61B 6/5211; G06T 7/0012; G06T 2207/10072; G06T 2207/10116; G06T 2207/20081; G06T 2207/30021; G06T 2207/30061; G06T 7/10; G16H 30/40; G16H 50/20
See application file for complete search history.

(56) References Cited

U.S. PATENT DOCUMENTS

| | | |
|---|---|---|
| 2012/0046971 A1 | 2/2012 | Walker et al. |
| 2018/0055577 A1* | 3/2018 | Barral .................... B25J 9/1633 |
| 2020/0085528 A1* | 3/2020 | Olson .................... A61B 90/36 |

OTHER PUBLICATIONS

Hyunkwang Lee, Mohammad Mansouri, Shahein Tajmir, Michael H. Lev, & Synho Do: "A Deep-Learning System for Fully-Automated Peripherally Inserted Central Catheter (PICC) Tip Detection", Oct. 5, 2017, Society for Imaging Informatics in Medicine 2017, pp. 1-11. (Year: 2017).*

Paras Lakhani, "Deep Convolutional Neural Networks for Endotracheal Tube Position and X-ray Image Classification: Challenges and Opportunities", J Digit Imaging, vol. 30, 2017, pp. 460-468.

* cited by examiner

METHOD AND SYSTEM FOR DETERMINING ABNORMALITY IN MEDICAL DEVICE

CROSS-REFERENCE TO RELATED APPLICATION

The present application is a continuation of International Patent Application No. PCT/KR2021/006163, filed May 17, 2021, which is based upon and claims the benefit of priority to Korean Patent Application No. 10-2020-0059347, filed on May 18, 2020 and Korean Patent Application No. 10-2021-0063464, filed on May 17, 2021. The disclosures of the above-listed applications are hereby incorporated by reference herein in their entirety.

TECHNICAL FIELD

The present disclosure relates to a method and a system for determining an abnormality in a medical device, and specifically, to a method and a system for determining an abnormality in a medical device included in a medical image.

BACKGROUND

In general, a doctor may use a medical image to determine a condition of a patient. For example, the doctor may check, through the medical image, the position, size, and shape of a lesion of the patient, and also the position of the medical device inserted into the body of the patient or placed outside the patient, and the like, and perform necessary diagnosis and treatment. In particular, for the required diagnosis and treatment, it is very important to determine whether or not the medical device is in a normal position and the like.

Meanwhile, the normal position of the medical device may be determined according to the type of the medical device, the anatomical position of the human body organ, and the like. In other words, the normal position of the medical device may be determined differently for each patient according to the type of the medical device, the position and size of the body organs, and the like. Accordingly, it may not be easy for the doctor to determine the normal position of the medical device based on the medical image of the patient. In particular, for patients with multiple complex findings, it may be difficult for the doctor to determine, based on the medical image, whether or not the medical device is in the normal position.

SUMMARY

In order to solve the problems described above, the present disclosure provides a method, a non-transitory computer-readable recording medium storing instructions, and an apparatus (system) for determining an abnormality in a medical device from a medical image.

The present disclosure may be implemented in various ways, including a method, a system (apparatus), and a computer-readable storage medium stored with a computer program.

According to an embodiment of the present disclosure, a method for determining an abnormality in a medical device in medical image is provided, which may be executed by at least one processor and include receiving a medical image, and detecting information on at least a part of a target medical device included in the received medical image.

According to an embodiment of the present disclosure, the detecting may include detecting the information on a position of the at least the part of the target medical device in the received medical image by using a first machine learning model.

According to an embodiment of the present disclosure, the method may further includes acquiring a plurality of reference medical images including one or more reference medical devices, and acquiring an annotation for a position of at least a part of the one or more reference medical devices included in the plurality of reference medical images. The first machine learning model may be trained to receive the plurality of reference medical images, and detect information on the reference medical devices included in each of the plurality of reference medical images based on the annotation for the position of at least the part of the one or more reference medical devices.

According to an embodiment of the present disclosure, the detecting the information on the position of the at least the part of the target medical device may include determining whether or not the target medical device is included in the received medical image by using a second machine learning model, and if the target medical device is included in the received medical image, detecting the information on the position of the at least the part of the target medical device in the received medical image by using the first machine learning model.

According to an embodiment of the present disclosure, the determining whether or not the target medical device is included in the received medical image by using the second machine learning model may include determining whether or not a medical device included in the received medical image belongs to the same medical device group as the target medical device. The second machine learning model is trained to receive a plurality of reference medical images and output a medical device group to which a reference medical device included in each of the plurality of reference medical images belongs.

According to an embodiment of the present disclosure, the detecting may include extracting, from the received medical image, a fiducial marker associated with the target medical device, and determining presence or absence of an abnormality in the target medical device based on the information on the target medical device and the extracted fiducial marker.

According to an embodiment of the present disclosure, the extracting may include extracting, from the received medical image, a fiducial marker associated with the target medical device by using a third machine learning model.

According to an embodiment of the present disclosure, the method may further include acquiring a plurality of reference medical images including one or more reference medical devices, and acquiring an annotation for a reference fiducial marker associated with the one or more reference medical devices included in the plurality of reference medical images. The third machine learning model may be trained to receive the plurality of reference medical images, and extract the reference fiducial marker associated with the one or more reference medical devices in the plurality of reference medical images based on the annotation for the reference fiducial marker associated with the one or more reference medical devices.

According to an embodiment of the present disclosure, the determining may include determining a normal area of the target medical device based on the extracted fiducial marker, and determining whether or not the at least the part of the target medical device is positioned in the normal area.

According to an embodiment of the present disclosure, a method for determining an abnormality in a medical device in medical imaging is provided, which may be executed by at least one processor and include receiving a reference medical image, determining a normal area associated with a reference medical device in the reference medical image, generating a first set of training data in which at least a part of the reference medical device is placed in the determined normal area in the reference medical image, generating a second set of training data in which the at least the part of the reference medical device is placed in an area other than the determined normal area in the reference medical image, and training a fourth machine learning model for determining presence or absence of an abnormality in the reference medical device based on the first set of training data and the second set of training data.

According to an embodiment of the present disclosure, the method may include receiving a medical image, and determining presence or absence of an abnormality in a target medical device included in the medical image by using a fourth machine learning model.

According to an embodiment of the present disclosure, the determining may include receiving, from an external device, information on the normal area associated with the position of the at least the part of the reference medical device, and applying a normal area associated with the position of the at least the part associated with the reference medical device to the reference medical image.

According to an embodiment of the present disclosure, the determining may include receiving, from an external device, information on a reference medical device for generating the training data, and extracting normal area associated with the reference medical device from in the reference medical image, based on the received information on the reference medical device and the information on the reference medical image.

According to an embodiment of the present disclosure, the fourth machine learning model includes a binary classification model trained to classify the reference medical image into normal data or abnormal data.

A non-transitory computer-readable recording medium storing instructions that, when executed by one or more processors, cause performance of the method described above according to the embodiment.

An information processing system according to another embodiment of the present disclosure is provided, which may include a memory storing one or more instructions, and a processor configured to execute the stored one or more instructions to receive a medical image and detect information on at least a part of a target medical device included in the received medical image.

An information processing system according to another embodiment of the present disclosure is provided, which may include a memory storing one or more instructions, and a processor configured to execute the stored one or more instructions to receive a reference medical image, determine a normal area associated with a reference medical device in the reference medical image, generate a first set of training data in which at least a part of the reference medical device is placed in the determined normal area in the reference medical image, generate a second set of training data in which the at least the part of the reference medical device is placed in an area other than the determined normal area in the reference medical image, and train a fourth machine learning model for determining presence or absence of an abnormality in the reference medical device based on the first set of training data and the second set of training data.

According to some embodiments of the present disclosure, user may easily acquire information on the presence or absence of an abnormality in the medical device associated with a patient in the medical image, since the information on the presence or absence of an abnormality is determined from the medical image. In particular, even in the case of a patient accompanied by several complex findings, the information on the presence or absence of an abnormality in the medical device can be acquired from the medical image.

According to some embodiments of the present disclosure, after a procedure of inserting the medical device into a body or attaching it to a body surface of the patient, the user can quickly and accurately check whether or not the procedure is performed correctly. Accordingly, if the inserted medical device is incorrectly positioned or the operation is not performed correctly, the user can take quick action.

According to some embodiments of the present disclosure, even when it is difficult to collect a large amount of medical images showing the medical device placed normally or abnormally, by generating a plurality of training medical images, it is possible to effectively train an artificial neural network model for determining the presence or absence of an abnormality in the medical device.

The effects of the present disclosure are not limited to the effects described above, and other effects not mentioned will be able to be clearly understood by those of ordinary skill in the art (referred to as "those skilled in the art") from the description of the claims.

BRIEF DESCRIPTION OF THE DRAWINGS

The above and other objects, features and advantages of the present disclosure will become more apparent to those of ordinary skill in the art by describing in detail exemplary embodiments thereof with reference to the accompanying drawings.

DETAILED DESCRIPTION

Figure 1:
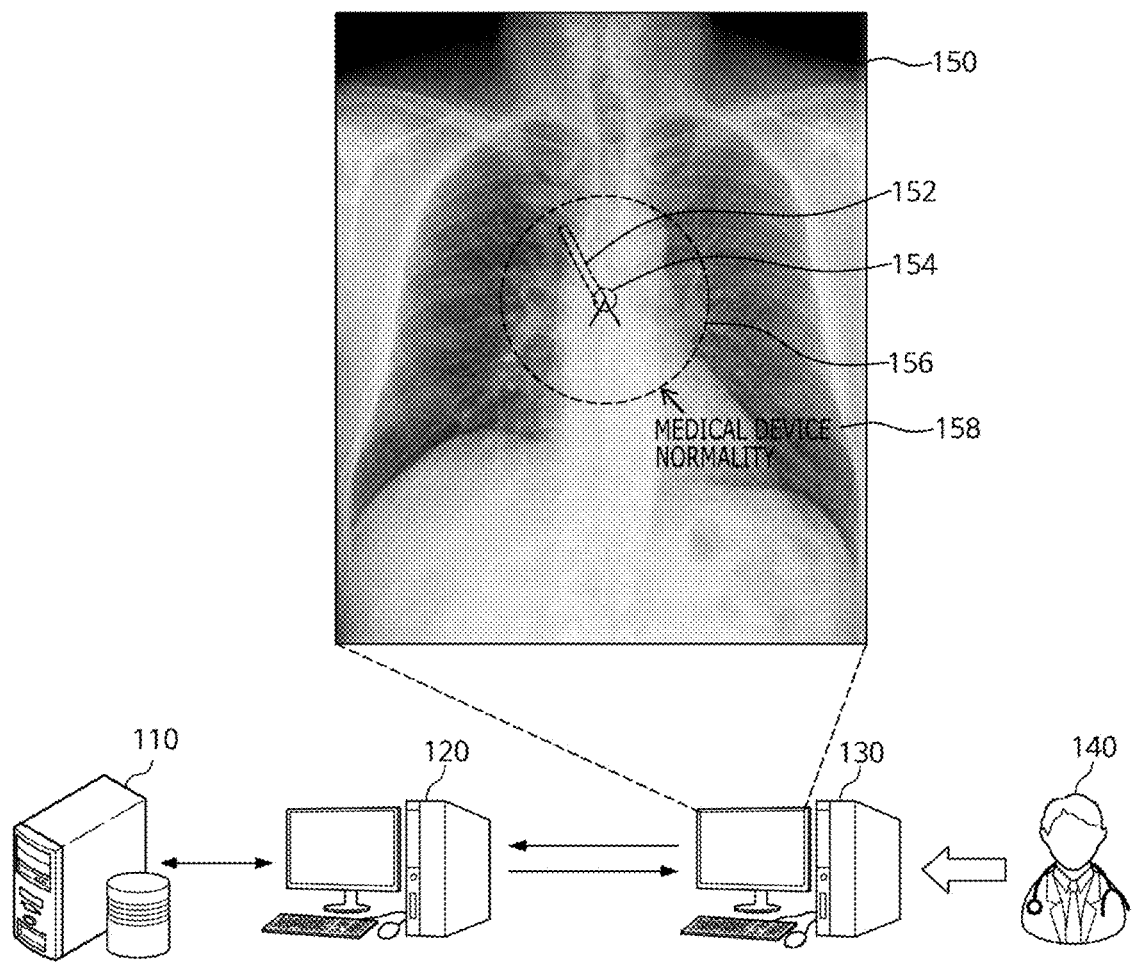
FIG. 1 is an exemplary configuration diagram illustrating an information processing system for providing information on a medical device according to an embodiment of the present disclosure.

Hereinafter, specific details for the practice of the present disclosure will be described in detail with reference to the accompanying drawings. However, in the following description, detailed descriptions of well-known functions or configurations will be omitted if it may make the subject matter of the present disclosure rather unclear.

In the accompanying drawings, the same or corresponding components are assigned the same reference numerals. In addition, in the following description of the embodiments, duplicate descriptions of the same or corresponding components may be omitted. However, even if descriptions of components are omitted, it is not intended that such components are not included in any embodiment.

Advantages and features of the disclosed embodiments and methods of accomplishing the same will be apparent by referring to embodiments described below in connection with the accompanying drawings. However, the present disclosure is not limited to the embodiments disclosed below, and may be implemented in various forms different from each other, and the present embodiments are merely provided to make the present disclosure complete, and to fully disclose the scope of the disclosure to those skilled in the art to which the present disclosure pertains.

The terms used herein will be briefly described prior to describing the disclosed embodiments in detail. The terms used herein have been selected as general terms which are widely used at present in consideration of the functions of the present disclosure, and this may be altered according to the intent of an operator skilled in the art, related practice, or introduction of new technology. In addition, in specific cases, certain terms may be arbitrarily selected by the applicant, and the meaning of the terms will be described in detail in a corresponding description of the embodiments. Therefore, the terms used in the present disclosure should be defined based on the meaning of the terms and the overall content of the present disclosure rather than a simple name of each of the terms.

As used herein, the singular forms "a," "an," and "the" are intended to include the plural forms as well, unless the context clearly indicates the singular forms. Further, the plural forms are intended to include the singular forms as well, unless the context clearly indicates the plural forms. Further, throughout the description, if a portion is stated as "comprising (including)" a component, it intends to mean that the portion may additionally comprise (or include or have) another component, rather than excluding the same, unless specified to the contrary.

Further, the term "module" or "unit" used herein refers to a software or hardware component, and "module" or "unit" performs certain roles. However, the meaning of the "module" or "unit" is not limited to software or hardware. The "module" or "unit" may be configured to be in an addressable storage medium or configured to play one or more processors. Accordingly, as an example, the "module" or "unit" may include components such as software components, object-oriented software components, class components, and task components, and at least one of processes, functions, attributes, procedures, subroutines, program code segments, drivers, firmware, micro-codes, circuits, data, database, data structures, tables, arrays, and variables. Furthermore, functions provided in the components and the "modules" or "units" may be combined into a smaller number of components and "modules" or "units", or further divided into additional components and "modules" or "units."

According to an embodiment, the "module" or "unit" may be implemented as a processor and a memory. The "processor" should be interpreted broadly to encompass a general-purpose processor, a central processing unit (CPU), a microprocessor, a digital signal processor (DSP), a controller, a microcontroller, a state machine, and so forth. Under some circumstances, the "processor" may refer to an application-specific integrated circuit (ASIC), a programmable logic device (PLD), a field-programmable gate array (FPGA), and so on. The "processor" may refer to a combination for processing devices, e.g., a combination of a DSP and a microprocessor, a combination of a plurality of microprocessors, a combination of one or more microprocessors in conjunction with a DSP core, or any other combination of such configurations. In addition, the "memory" should be interpreted broadly to encompass any electronic component that is capable of storing electronic information. The "memory" may refer to various types of processor-readable media such as random access memory (RAM), read-only memory (ROM), non-volatile random access memory (NVRAM), programmable read-only memory (PROM), erasable programmable read-only memory (EPROM), electrically erasable PROM (EEPROM), flash memory, magnetic or optical data storage, registers, and so on. The memory is said to be in electronic communication with a processor if the processor can read information from and/or write information to the memory. The memory integrated with the processor is in electronic communication with the processor.

In the present disclosure, a "system" may include at least one of a server device and a cloud device, but not limited thereto. For example, the system may include one or more server devices. In another example, the system may include one or more cloud devices. In still another example, the system may include both the server device and the cloud device operated in conjunction with each other.

In the present disclosure, a "display" may refer to any display device associated with a computing device, and for example, it may refer to any display device that is controlled by the computing device, or that can display any information/data provided from the computing device.

In the present disclosure, the "artificial neural network model" is an example of the machine learning model, and may include any model used to infer an answer to a given input. According to an embodiment, the artificial neural network model may include an artificial neural network model including an input layer, a plurality of hidden layers, and an output layer. In an example, each layer may include one or more nodes. In addition, the artificial neural network model may include weights associated with a plurality of nodes included in the artificial neural network model. In an example, the weights may include any parameter that is associated with the artificial neural network model.

In the present disclosure, a "medical image" may refer to any image, picture, and the like associated with the medical field. In addition, the medical image may refer to an image or a picture obtained by capturing at least a part of a patient's body, and may include a 2D image, a 3D image, a synthetic image, and the like, captured in the form of X-ray, Computed Tomography (CT), Magnetic Resonance Imaging (MRI), Position Emission Tomography (PET), Single Photon Emission CT (SPECT), Digital Breast Tomosynthesis (DBT), and the like, for example. In addition, the "reference medical image" may refer to the medical image described above and which may be an image used for training any machine learning model. In the present disclosure, the medical image may refer to a reference medical image, or conversely, the reference medical image may refer to the medical image.

In the present disclosure, the "annotation" may refer to an annotation work and/or annotation information (e.g., label information, and the like) determined by performing the annotation work. In addition, the "annotation information" may refer to information for the annotation work and/or information (e.g., label information) generated by the annotation work. In the present disclosure, the annotation may be performed by image-level labeling, pixel-level labeling, or the like for, included in the medical image, the medical device (position, shape, the presence or absence of damage, and the like of the medical device), a fiducial marker (position, shape, and the like of the fiducial marker), a normal area (position, shape of the normal area, and the like) according to the fiducial marker, and the like. For example, the annotation may include a segmentation annotation. In an example, the segmentation annotation may refer to an annotation technique for classifying all pixels of an image into corresponding classes and then classifying and labeling objects in the image.

In the present disclosure, the "medical device" may refer to any medical instrument and device that is inserted into or attached to the body of a patient, and the medical device may include, for example, an endotracheal tube (E-tube), a nasogastric tube (N-tube), a central venous catheter, a pulmonary artery catheter (Swan-Ganz catheter), a chest tube, a pericardiocentesis tube, a Cardiac implantable electronic device (CIED), and the like. In addition, by "at least a part of the medical device," it may refer to a part of the medical device which is necessary for the determination of an abnormality in the medical device. In addition, by the "abnormality in the medical device," it may include the medical device (or a part of the medical device) being not positioned in the normal area, the medical device being damaged or broken, and the like. In an example, the "target medical device" refers to the medical device described above, which may be a medical device as a target of the abnormality determination, and the "reference medical device" may refer to the medical device described above, which may be a medical device included in the reference medical image used for training any machine learning model. In the present disclosure, the medical device may refer to the target medical device or the reference medical device, or conversely, the target medical device or the reference medical device may refer to the medical device.

In the present disclosure, the "normal area" may be an area of ideal position where the medical device should be positioned. For example, the normal area may be determined differently according to each medical device, anatomy of a body organ of the patient, and the like. Such a normal area may be determined from a fiducial marker, which may be displayed on the medical image in the form of, for example, a mask, an area, a contour, a line, a point, and the like in the medical image.

In the present disclosure, the "fiducial marker" is a marker that serves as a criterion for determining the normal area, and may be displayed in the form of a mask, an area, a contour, a line, a point, and the like in the medical image. For example, if the normal area is determined to be an area within a predetermined distance from the carina, the fiducial marker may be an area corresponding to the carina. In an example, the reference fiducial marker may refer to the fiducial marker described above, which may be a fiducial marker used for training any machine learning model. In the present disclosure, the fiducial marker may refer to the reference fiducial marker, or conversely, the reference fiducial marker may refer to the fiducial marker.

In the present disclosure, "instructions" may refer to one or more instructions grouped based on functions, which are the components of a computer program and executed by the processor.

FIG. 1 is an exemplary configuration diagram illustrating an information processing system 120 for providing information on a medical device according to an embodiment of the present disclosure. As illustrated, the information processing system 120 may be configured so as to be communicatively connected to each of a user terminal 130 and a storage system 110. While FIG. 1 is a diagram illustrating one user terminal 130, embodiments are not limited thereto, and in an exemplary configuration, a plurality of user terminals 130 may be connected to the information processing system 120 for communication. In addition, while the information processing system 120 is illustrated as one computing device in FIG. 1, embodiments are not limited thereto, and the information processing system 120 may be configured to process information and/or data in a distributed manner through a plurality of computing devices. In addition, while the storage system 110 is illustrated as a single device in FIG. 1, embodiments are not limited thereto, and the system may be configured with a plurality of storage devices or as a system that supports cloud. In addition, respective components of the system for providing information on the medical device illustrated in FIG. 1 represent functional components that can be divided on the basis of functions, and in an actual physical environment, a plurality of components may be implemented as being incorporated with each other.

The storage system 110 is a device or cloud system that stores and manages various data associated with a machine learning model for providing information on the medical device included in a medical image 150. For efficient data management, the storage system 110 may store and manage various types of data using a database. In an example, the various types of data may include any data associated with the machine learning model (e.g., weights, parameters, input and output values, and the like associated with the machine learning model). Furthermore, the data may include information on the medical device, information on the fiducial marker, information on the normal area, information indicating whether or not the medical device is positioned in the normal area, information indicating the presence or absence of damage in the medical device, and the like, but embodiments are not limited thereto. While FIG. 1 shows the information processing system 120 and the storage system 110 as separate systems, embodiments are not limited thereto, and they may be incorporated into one system.

The information processing system 120 and/or the user terminal 130 are any computing devices that are used to provide information on the medical device included in the medical image. In an example, the computing device may refer to any type of device equipped with a computing function, and may be a notebook, a desktop, a laptop, a tablet computer, a server, a cloud system, and the like, for example, but is not limited thereto. The information processing system 120 may output the medical image 150 to a display device of the user terminal 130 to provide a user 140 with the same. According to an embodiment of the present disclosure, the information processing system 120 may provide the user 140 with, through the user terminal 130, the medical image 150 including text, guide lines, indicators, and the like indicating whether or not the target medical device is included, a fiducial marker associated with the target medical device, whether or not the target medical device is positioned in the normal area, the presence or absence of damage in the target medical device, and the like.

According to an embodiment, the information processing system 120 may receive the medical image 150. In an example, the medical image 150 may refer to any image, picture, and the like associated with the medical field, and may include a 2D image, a 3D image, a synthetic image, and the like captured or generated in the form of X-ray, Computed Tomography (CT), Magnetic Resonance Imaging (MRI), Position Emission Tomography (PET), Single Photon Emission CT (SPECT), Digital Breast Tomosynthesis (DBT), and the like, for example. Such a medical image 150 may be directly captured by a device associated with the information processing system 120, or may be received from an external system (e.g., the user terminal 130, the storage system 110, and the like).

Then, the information processing system 120 may detect a target medical device 152 (or information on at least a part of the target medical device 152) included in the received medical image 150. In an example, the medical device may refer to any medical instrument or device that is inserted into or attached to the body of a patient. In addition, the information on the medical device (or information on at least a part of the medical device) may include information on a type, a name, and the like of the medical device that can specify the medical device included in the medical image 150, and information on a position, a shape, and a size of the specified medical device (or of at least a part of the medical device), the presence or absence of an abnormality in the medical device, the presence or absence of damage in the medical device, and/or a group in which the medical device is included, and the like. For example, the medical device may include an endotracheal tube (E-tube), a nasogastric tube (N-tube), a central venous catheter, a pulmonary artery catheter (Swan-Ganz catheter), a chest tube, a pericardiocentesis tube, a Cardiac implantable electronic device (CIED), and the like.

The information processing system 120 may extract a normal area 156 associated with the target medical device 152 from the received medical image 150. For example, the normal area 156 may be determined by a fiducial marker 154. In an example, the fiducial marker 154 may be a marker serving as a criterion for determining the normal area 156 associated with the target medical device 152, and may include at least one of a point, a line, and an area. In addition, the normal area 156 may be an area of ideal position where the target medical device 152 should be positioned. For example, the normal area of the endotracheal tube (the normal area where the tube tip of the endotracheal tube should be positioned) may be an area within the airway positioned about 5 cm above the keel (carina), which is the fiducial marker, and the normal area of the nasogastric tube may be a position lower than the diaphragm which is the fiducial marker, and the normal area of the central venous tube may be an area ranging from the superior vein to the right atrium of the heart. In addition, the normal area of the pulmonary artery catheter may be an area within the right or left pulmonary artery branching from the main pulmonary artery, the normal area of the chest tube may be an area within the chest tube, and the normal area of the pericardial puncture tube may be within the shadow of the heart. That is, if the target medical device 152 included in the medical image 150 is specified, the information processing system 120 may extract the fiducial marker 154 such as a position (anatomical position of a body organ), a size, and the like of a body organ for determining the normal area 156 of the target medical device 152, and extract the normal area 156 associated with the specific target medical device 152 through the fiducial marker 154 from the medical image 150.

The information processing system 120 may determine an abnormality in the target medical device 152 based on information on the medical device, the normal area 156, and the like. For example, the abnormality in the target medical device 152 may include the presence or absence of damage in the target medical device 152, whether or not the target medical device 152 is positioned on a normal area, and the like. According to an embodiment, the information processing system 120 may use a predetermined algorithm, a machine learning model, and the like, to determine whether or not the target medical device 152 is damaged, whether or not the target medical device 152 is positioned on the normal area, and the like, based on information on the target medical device 152, the normal area 156, and the like.

The information processing system 120 may determine whether or not at least a part of the target medical device 152 is positioned on the normal area 156. According to an embodiment, the information processing system 120 may determine whether or not at least a part of the target medical device 152 is positioned on the normal area 156 based on a plurality of predetermined rules. In an example, the plurality of predetermined rules may be determined for each medical device. For example, a rule associated with an endotracheal tube may be determined as "the tube tip should be positioned in an area within the airway positioned between 5 cm and 7 cm above the keel". Additionally or alternatively, the plurality of predetermined rules may be determined for each of a plurality of medical devices belonging to the same group. That is, by using the predetermined rule, the information processing system 120 may extract information 158 (e.g., text, image, guide line, indicator, and the like) on whether or not the target medical device 152 is positioned in the normal area 156, and display the information on the medical image 150. Additionally or alternatively, the information processing system 120 may use any machine learning model to determine whether or not at least a part of the target medical device 152 is positioned on the normal area 156.

According to another embodiment, the information processing system 120 may use a trained machine learning model to determine the presence or absence of an abnormality in the target medical device 152 included in the medical image 150. In other words, the information processing system 120 may detect the target medical device 152, and input the medical image 150 into the trained machine learning model without extracting the normal area 156, to determine the presence or absence of an abnormality in the target medical device 152.

FIG. 1 illustrates that a text ("medical device normality") indicating the presence or absence of an abnormality in the target medical device 152 is displayed together with a guide line (arrow) on the right side of the normal area 156 in the medical image 150, but embodiments are not limited thereto, and the information 158 on whether or not the target medical device 152 is positioned in the normal area 156 may be displayed in any area of the medical image 150. In addition, FIG. 1 illustrates that a dotted line box indicating the target medical device 152 and the normal area 156 is displayed on the medical image 150, but the dotted line box indicating the target medical device 152 and the normal area 156 may not be displayed and omitted. In addition, FIG. 1 illustrates that whether or not the target medical device 152 is positioned in the normal area 156 is displayed on the medical image 150, but embodiments are not limited thereto, and the presence or absence of damage in the medical device may be displayed in the medical image 150. With such a configuration, even for a patient with various complex findings, the user 140 may easily acquire the information on the presence or absence of an abnormality in the medical device determined based on the medical image 150 through the information processing system 120. In addition, after a procedure of inserting the medical device into a body or attaching it to a body surface of the patient, the user 140 can quickly and accurately check whether or not the procedure is performed correctly.

Figure 2:
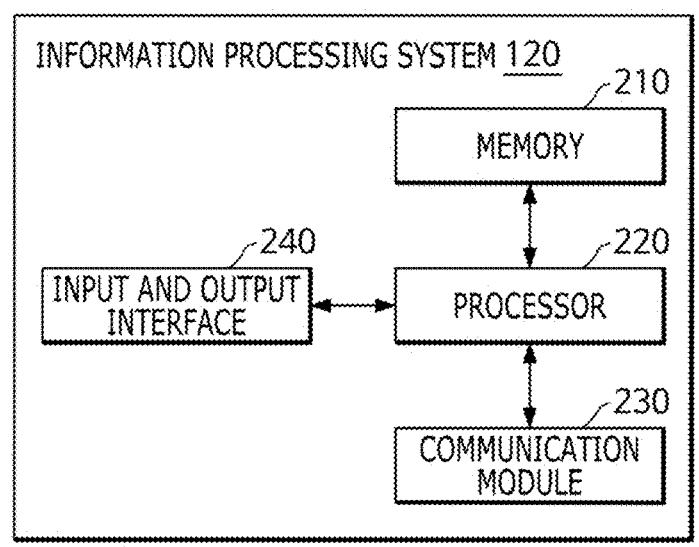
FIG. 2 is a block diagram of an internal configuration of an information processing system according to an embodiment of the present disclosure.

FIG. 2 is a block diagram of an internal configuration of the information processing system 120 according to an embodiment of the present disclosure. The information processing system 120 may include a memory 210, a processor 220, a communication module 230, and an input and output interface 240. As illustrated in FIG. 2, the information processing system 120 may be configured to communicate information and/or data through a network by using the communication module 230.

The memory 210 may include any non-transitory computer-readable recording medium. According to an embodiment, the memory 210 may include a permanent mass storage device such as random access memory (RAM), read only memory (ROM), disk drive, solid state drive (SSD), flash memory, and so on. In another example, a non-destructive mass storage device such as ROM, SSD, flash memory, disk drive, and so on may be included in the information processing system 120 as a separate permanent storage device that is distinct from the memory. In addition, the memory 210 may store an operating system and at least one program code (e.g., code installed and driven in the information processing system 120 to detect information on at least a part of a medical device, extract a fiducial marker, extract a normal area, determine whether or not the medical device is positioned in the normal area, determine the presence or absence of damage in the medical device, and the like).

These software components may be loaded from a computer-readable recording medium separate from the memory 210. Such a separate computer-readable recording medium may include a recording medium directly connectable to the information processing system 120, and may include a computer-readable recording medium such as a floppy drive, a disk, a tape, a DVD/CD-ROM drive, a memory card, and the like, for example. In another example, the software components may be loaded into the memory 210 through the communication module 230 rather than the computer-readable recording medium. For example, at least one program may be loaded into the memory 210 based on a computer program (e.g., a program for detecting information on at least a part of the medical device, extracting a fiducial marker, extracting a normal area, determining whether or not the medical device is positioned in the normal area, and the like) which is installed by the files provided by the developers, or by a file distribution system that distributes an installation file of an application through the communication module 230.

The processor 220 may be configured to process the commands of the computer program by performing basic arithmetic, logic, and input and output operations. The commands may be provided to a user terminal (not illustrated) or another external system by the memory 210 or the communication module 230. For example, the processor 220 may receive a medical image, and detect information on at least a part of a target medical device included in the received medical image. For example, the processor 220 may detect information on the position of at least a part of the target medical device in the received medical image. In addition, the processor 220 may extract a fiducial marker associated with the target medical device from the received medical image. Then, the processor 220 may determine the presence or absence of an abnormality in the target medical device based on the information on the target medical device and the extracted fiducial marker. In this case, the processor 220 may determine a normal area of the target medical device based on the extracted fiducial marker, and determine whether or not at least a part of the target medical device is positioned in the normal area. The processor 220 may display the information on whether or not the target medical device is positioned on the normal area, on the medical image in a predetermined form (e.g., text, image, guide line, indicator, and the like).

The communication module 230 may provide a configuration or function for the user terminal (not illustrated) and the information processing system 120 to communicate with each other through a network, and may provide a configuration or function for the information processing system 120 to communicate with an external system (e.g., a separate cloud system). For example, control signals, commands, data, and the like provided under the control of the processor 220 of the information processing system 120 may be transmitted to the user terminal and/or the external system through the communication module 230 and the network through the communication module of the user terminal and/or an external system. For example, the user terminal and/or the external system may receive, from the information processing system 120, the information on whether or not the target medical device is positioned in the normal area, the information on the presence or absence of damage in the target medical device, and the like.

In addition, the input and output interface 240 of the information processing system 120 may be a means for interfacing with a device (not illustrated) for inputting or outputting, which may be connected to the information processing system 120 or included in the information processing system 120. In FIG. 2, the input and output interface 240 is illustrated as a component configured separately from the processor 220, but embodiments are not limited thereto, and the input and output interface 240 may be configured to be included in the processor 220. The information processing system 120 may include more components than those illustrated in FIG. 2. Meanwhile, most of the related components may not necessarily require exact illustration.

The processor 220 of the information processing system 120 may be configured to manage, process, and/or store the information and/or data received from a plurality of user terminals and/or a plurality of external systems. According to an embodiment, the processor 220 may receive the medical image from the user terminal and/or the external system. In this case, the processor 220 may detect the information on at least a part of the target medical device included in the received medical image.

Figure 3:
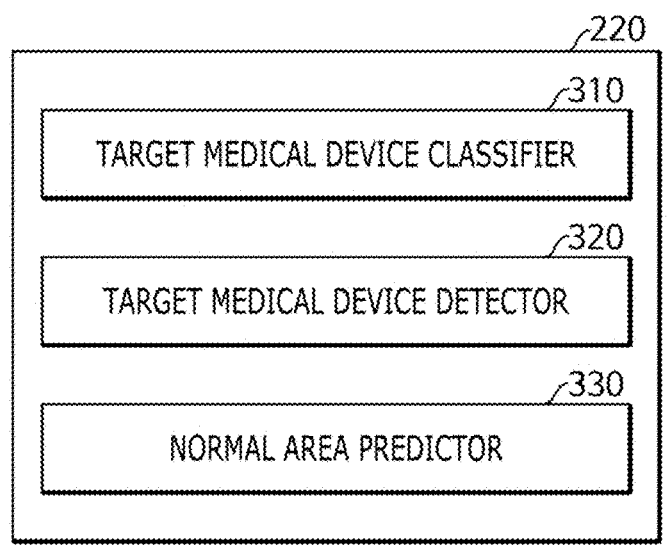
FIG. 3 is a functional block diagram of an internal configuration of a processor according to an embodiment of the present disclosure.

FIG. 3 is a functional block diagram of an internal configuration of the processor 220 according to an embodiment of the present disclosure. As illustrated, the processor 220 may include a target medical device classifier 310, a target medical device detector 320, a normal area predictor 330, and the like. In this case, the processor 220 may communicate with a database and/or an external device (e.g., a user terminal or an external system) that includes medical images, and receive a medical image necessary for determining an abnormality in the medical device.

The target medical device classifier 310 may determine whether or not a target medical device is included in the received medical image. According to an embodiment, the target medical device classifier 310 may determine whether or not the medical device included in the received medical image belongs to the same medical device group as the target medical device. To this end, the target medical device classifier 310 may group a plurality of medical devices for determining abnormalities in the medical devices. For example, the target medical device classifier 310 may use a grouping algorithm, a machine learning model, or the like to group medical devices into a group that can be determined for the presence or absence of an abnormality based on one criterion.

According to an embodiment, the target medical device classifier 310 may include a machine learning model trained to detect to which group the medical device included in the medical image belongs. In this case, the target medical device classifier 310 may be trained to receive a plurality of reference medical images and output a medical device group to which a reference medical device included in each of the plurality of reference medical images belongs. In this case, the target medical device classifier 310 may be trained with the annotated training data. For example, the processor 220 may collect a medical image that includes a medical device (or a group to which the medical device belongs) to be determined, and a medical image that does not include a medical device (or a group to which the medical device belongs) to be determined. Then, if there is a medical device to be determined in the medical image, the processor 220 may perform labeling (e.g., image level labeling, pixel level labeling, and the like) on the corresponding medical device, and if there is no medical device to be determined, label 0 to perform annotation. By using the annotated medical image as described above, the processor 220 may train the target medical device classifier 310.

According to an embodiment, if a medical image is received, the target medical device classifier 310 may crop or divide only an area in the medical image in which the medical device to be determined is present. Then, the target medical device classifier 310 may also detect the presence or absence of the target medical device in the divided medical image. Additionally or alternatively, the target medical device classifier 310 may detect only a part of the target medical device (e.g., a tube tip, and the like).

The target medical device detector 320 may detect the information on the position of at least a part of the target medical device in the received medical image. For example, the target medical device detector 320 may detect the position of the whole or part of the target medical device classified or detected by the target medical device classifier 310. Additionally, the target medical device detector 320 may further detect the information on the size, the shape, and the like of the target medical device. In this case, the position, the size, the shape, and the like of the target medical device may be the information calculated based on the number of pixels in the medical image, or the information calculated based on the relative relationship (relative position, size, and the like) with other body organs and the like included in the medical image.

According to an embodiment, the target medical device detector 320 may include a machine learning model trained to detect the information on the position of at least a part of the target medical device included in the received medical image. In this case, the target medical device detector 320 may be trained with the annotated training data. For example, the processor 220 may acquire a plurality of reference medical images that include one or more reference medical devices, and acquire an annotation for the position of at least a part of one or more reference medical devices included in the plurality of reference medical images. In this case, the target medical device detector 320 may be trained to receive the plurality of reference medical images, and detect the information on the reference medical devices included in each of the plurality of reference medical images based on the annotation for the position of at least a part of the one or more reference medical devices. For example, the processor 220 may label the position, the size, the shape, and the like of the medical device (or a part of the medical device) in the medical image including the medical device to perform annotation. In an example, the annotation may be performed in the form of a mask, an area, a contour, a line, a point, and the like, indicating the information on the medical device. In this case, the annotation may be respectively performed for each type of medical device included in the medical image, or may be performed irrespective of the type. Then, the processor 220 may train the target medical device detector 320 using the annotated medical image as described above.

The normal area predictor 330 may extract a fiducial marker associated with the target medical device from the received medical image. In addition, the normal area predictor 330 may determine the normal area of the target medical device based on the extracted fiducial marker. For example, the normal area predictor 330 may extract a fiducial marker associated with the medical device classified or detected by the target medical device classifier 310. In addition, the normal area predictor 330 may determine the normal area based on the extracted fiducial marker. In this case, the normal area predictor 330 may determine the normal area from the fiducial marker based on a predetermined criterion (a criterion according to the corresponding medical device or group of medical devices). For example, if the endotracheal tube is the detected medical device, the normal area predictor 330 may extract a keel (carina) area as a fiducial marker for the endotracheal tube. Then, the normal area predictor 330 may extract an area in the airway near the area 5 cm above the keel area as the normal area. That is, the normal area may be determined differently according to medical devices, positions of body organs of a patient included in the medical image, and the like. In FIG. 3, it has been described above that the normal area predictor 330 extracts the fiducial marker and determines the normal area based on the fiducial marker, but embodiments are not limited thereto, and the normal area predictor 330 may be divided into two or more modules, such as a module for extracting a fiducial marker and a module for determining a normal area.

According to an embodiment, the normal area predictor 330 may include a machine learning model trained to extract a fiducial marker associated with a target medical device from a received medical image. In this case, the normal area predictor 330 may be trained with the annotated training data. For example, the processor 220 may acquire a plurality of reference medical images that include one or more reference medical devices, and acquire an annotation for a reference fiducial marker associated with one or more reference medical devices included in the plurality of reference medical images. That is, the processor 220 may label a fiducial marker associated with the medical device in the medical image for each type of medical device or for each group to which each medical device belongs and perform annotation. In an example, the annotation may be performed in the form of a mask, an area, a contour, a line, a point, or the like that indicates the fiducial marker. In this case, the normal area predictor 330 may be trained to receive the plurality of reference medical images, and extract a reference fiducial marker associated with the one or more reference medical devices in the plurality of reference medical images based on the annotation for the reference fiducial marker associated with the one or more reference medical devices. In FIG. 3, it has been described above that the normal area predictor 330 first extracts the fiducial marker and then determines the normal area associated with the medical device based on the fiducial marker, but embodiments are not limited thereto, and the normal area predictor 330 may directly determine, or be trained to determine, the normal area associated with the medical device without first extracting the fiducial marker.

According to an embodiment, the processor 220 may determine the presence or absence of an abnormality, that is, it 220 may determine, for example, whether or not at least a part of the target medical device is positioned in the normal area and the like, using the information on the position of at least a part of the medical device extracted by the target medical device detector 320, and the fiducial marker and/or the normal area extracted by the normal area predictor 330. For example, the processor 220 may determine the presence or absence of an abnormality using a predetermined rule, or may determine the presence or absence of an abnormality using a machine learning model. Then, the processor 220 may display information associated with the determined presence or absence of an abnormality in association with the medical image. For example, the information associated with the presence or absence of an abnormality may be displayed using text, image, guide line, indicator, and the like.

Additionally or alternatively, training data for training the target medical device classifier 310, the target medical device detector 320, and the normal area predictor 330 may be generated by the processor 220. For example, the processor 220 may receive a reference medical image that does not include a medical device. In addition, the processor 220 may determine, in the reference medical image, a reference medical device for generating training data, and a normal area associated with the reference medical device. Then, the processor 220 may display at least a part of the reference medical device in the determined normal area in the reference medical image to generate a first set of training data in which the reference medical device is normally positioned. In addition, the processor 220 may display at least a part of the reference medical device in an area other than the determined normal area in the reference medical image to generate a second set of training data in which the reference medical device is abnormally positioned. In this case, the processor 220 may train the target medical device classifier 310, the target medical device detector 320 and/or the normal area predictor 330 based on the generated first set of training data and second set of training data. Additionally or alternatively, the processor 220 may train any machine learning model that receives the medical image and outputs the presence or absence of an abnormality in the medical device, based on the generated first set of training data and second set of training data and. With this configuration, the processor 220 can efficiently generate a large amount of training data for training the machine learning model even in a situation where it is difficult to collect medical images associated with the medical device.

Although the components of the processor 220 have been described separately for each function in FIG. 3, it does not necessarily mean that they are physically separated. For example, the target medical device detector 320 and the normal area predictor 330 have been described above as separate components, but this is for better understanding of the disclosure, and embodiments are not limited thereto. For example, the target medical device classifier 310, the target medical device detector 320, and the normal area predictor 330 may be implemented through one machine learning model, or may be implemented through a plurality of different machine learning models. In addition, while FIG. 3 illustrates that there is an abnormality in the medical device if the medical device is not positioned on the normal area, but embodiments are not limited thereto, and it may also be determined that there is an abnormality in the medical device if the medical device is damaged.

Figure 4:
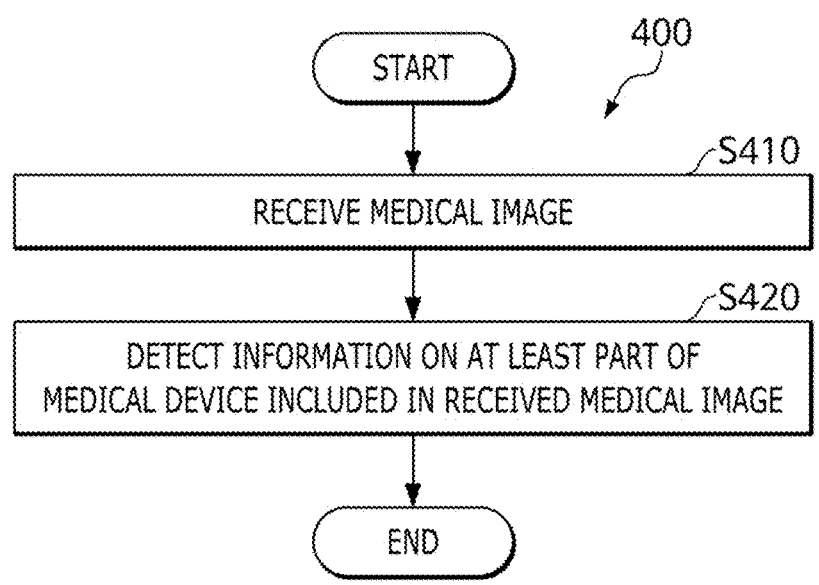
FIG. 4 is a flowchart illustrating a method for determining an abnormality in a medical device according to an embodiment of the present disclosure.

FIG. 4 is a flowchart illustrating a method 400 for determining an abnormality in the medical device according to an embodiment of the present disclosure. According to an embodiment, the method 400 for determining an abnormality in the medical device may be performed by a processor (e.g., a processor of the user terminal and/or at least one processor of the information processing system). As illustrated, the method 400 for determining an abnormality in the medical device may be initiated by the processor receiving a medical image (S410). For example, the processor may directly capture the medical images using any device associated with the information processing system, or receive the medical images from an external device (e.g., user terminal or database).

The processor may detect the information on at least a part of the target medical device included in the received medical image (S420). In an example, the information on at least a part of the medical device may include a position of the whole or part of the medical device, information on a group to which the medical device belongs, whether or not the medical device corresponds to the target medical device, and the like. The processor may use the first machine learning model to detect the information on the position of at least a part of the target medical device in the received medical image. In this case, the processor may acquire a plurality of reference medical images that include one or more reference medical devices, and acquire an annotation for the position of at least a part (e.g., tube tip, whole tube) of the one or more reference medical devices included in the plurality of reference medical images. In this case, the first machine learning model may be trained to receive the plurality of reference medical images, and detect the information on the reference medical devices included in each of the plurality of reference medical images based on the annotation for the position of at least a part of the one or more reference medical devices.

According to an embodiment, the processor may use the second machine learning model to determine whether or not the target medical device is included in the received medical image. If the target medical device is included in the received medical image, the processor may use the first machine learning model to detect the information on the position of at least a part of the target medical device in the received medical image. In this case, the first machine learning model and the second machine learning model may be integrated. For example, the processor may determine whether or not the medical device included in the received medical image belongs to the same medical device group as the target medical device. In an example, the second machine learning model may be trained to receive a plurality of reference medical images and output a medical device group to which the reference medical device included in each of the plurality of reference medical images belongs.

In order to detect the information on at least a part of the target medical device, the processor may extract a fiducial marker associated with the target medical device from the received medical image, and determine the presence or absence of an abnormality in the target medical device based on the information on the target medical device and the extracted fiducial marker. For example, the presence or absence of an abnormality in the target medical device may include malposition of the target medical device, damage to the target medical device itself, and the like. In this case, the processor may use the third machine learning model to extract the fiducial marker associated with the target medical device from the received medical image. For example, the processor may acquire a plurality of reference medical images that include one or more reference medical devices, and acquire an annotation for the reference fiducial marker associated with one or more reference medical devices included in the plurality of reference medical images. In this case, the third machine learning model may be trained to receive the plurality of reference medical images, and extract a reference fiducial markers associated with the one or more reference medical devices in the plurality of reference medical images based on the annotation for the reference fiducial marker associated with the one or more reference medical devices.

Figure 5:
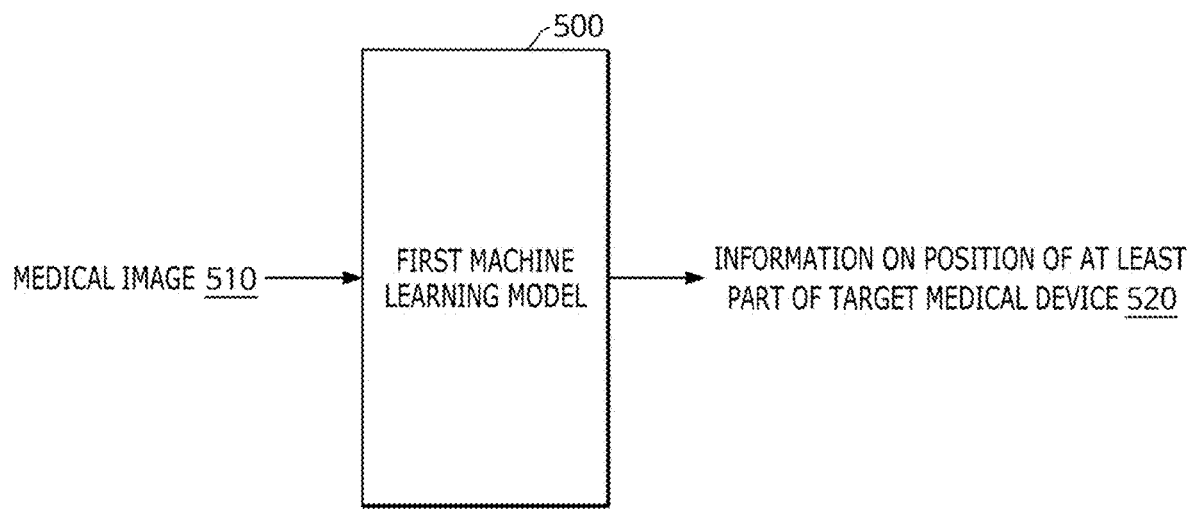
FIG. 5 is a diagram illustrating an example of a first machine learning model according to an embodiment of the present disclosure.

FIG. 5 illustrates an example of a first machine learning model 500 according to an embodiment of the present disclosure. As illustrated, the first machine learning model 500 may receive a medical image 510 and output information 520 on a position of at least a part of a target medical device included in the medical image 510. For example, the first machine learning model 500 may be accessed by or included in the target medical device detector (320 of FIG. 3) described above.

According to an embodiment, the first machine learning model 500 may be trained to receive the plurality of reference medical images, and detect the information on the reference medical devices included in each of the plurality of reference medical images based on the annotation for the position of at least a part of the one or more reference medical devices. For example, in order to generate and train the first machine learning model 500, the processor (220 of FIG. 2) may acquire a plurality of reference medical images that include the reference medical device, and acquire annotation information on the position of at least a part of the reference medical devices included in the plurality of reference medical images.

Then, the processor may use the information on the position of at least a part of the annotated reference medical device as ground truth when training the first machine learning model 500. For example, the annotation may be performed by image-level labeling, pixel-level labeling, and the like, and may include segmentation annotation. In an example, the segmentation annotation may refer to an annotation technique for classifying at least some pixels of an image into corresponding classes and then classifying and labeling the objects in the image. That is, if the first machine learning model 500 detects at least a part of the target medical device, the first machine learning model 500 may use anatomical segmentation to recognize the determination of abnormality of the target medical device in and/or outside the body.

Additionally or alternatively, the processor may generate training data for training the first machine learning model 500 by using a medical image that does not include the medical device. For example, the processor may determine, in the reference medical image, a reference medical device for generating training data, and a normal area associated with the reference medical device. Then, the processor may display at least a part of the reference medical device in the determined normal area in the reference medical image to generate a first set of training data in which the reference medical device is normally positioned, and display at least a part of the reference medical device in an area other than the determined normal area in the reference medical image to generate a second set of training data in which the reference medical device is abnormally positioned. In this case, the first machine learning model 500 may be trained with the generated first set of training data and second set of training data.

Additionally or alternatively, the first machine learning model 500 may be trained based on information on a lesion included in the reference medical image. According to an embodiment, if the information on a lesion is recognized, the first machine learning model 500 may infer the information on the medical device used in relation to the lesion with an increased accuracy. For example, the first machine learning model 500 may be trained to receive a plurality of reference medical images, and detect the information on the medical device related to a lesion included in each of a plurality of reference medical images based on the annotation for one or more lesions (position, size, shape, and the like of the lesions). For example, in order to generate and train the first machine learning model 500, the processor may acquire a plurality of reference medical images including lesions, and acquire annotations for the lesions included in the plurality of reference medical images. According to another embodiment, the processor may select a lesion detection learning model as an initial model for the first machine learning model 500, and train the first machine learning model 500 to infer the information on the position of at least a part of the target medical device in the medical image. In this way, if the lesion detection learning model is selected as the initial model for training the first machine learning model 500, a higher accuracy can be provided compared to when a different model is selected as the initial model.

Figure 6:
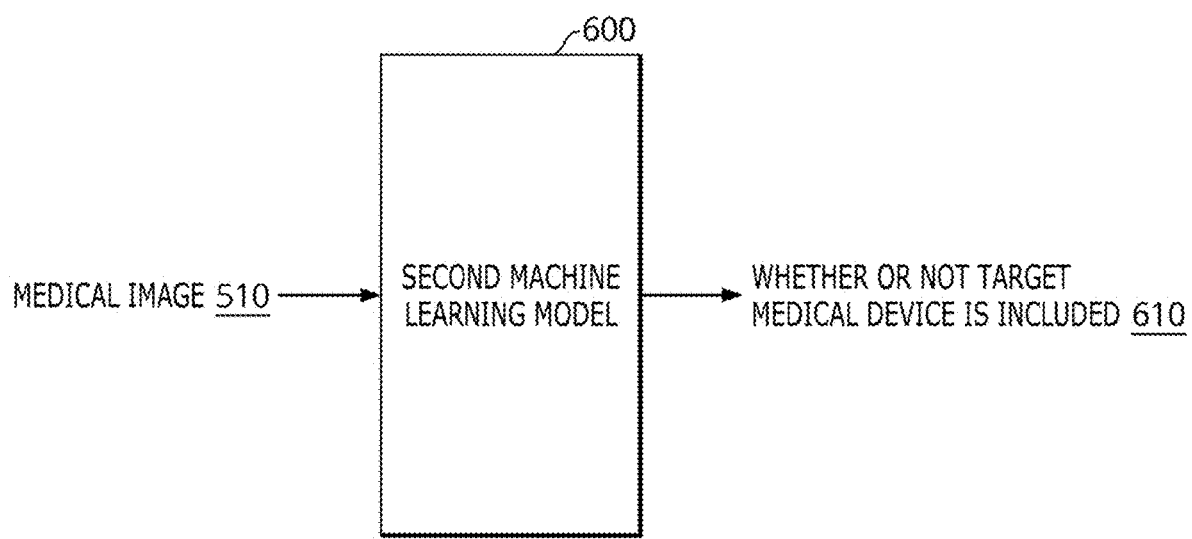
FIG. 6 is a diagram illustrating an example of a second machine learning model according to an embodiment of the present disclosure.

FIG. 6 illustrates an example of a second machine learning model 600 according to an embodiment of the present disclosure. As illustrated, the second machine learning model 600 may receive the medical image 510 and determine whether or not the target medical device is included (610) in the received medical image 510. For example, the second machine learning model 600 may be accessed by or included in the target medical device classifier (310 of FIG.

3) described above. In addition, whether or not the target medical device is included (610) may include whether or not the medical device included in the medical image 510 belongs to the same medical device group as the target medical device. Accordingly, the second machine learning model 600 may receive the medical image 510 and output information on the groups that the medical device included in the medical image 510 belongs.

According to an embodiment, the second machine learning model 600 may be trained to receive a plurality of reference medical images and output a medical device group to which a reference medical device included in each of the plurality of reference medical images belongs. In this case, the second machine learning model 600 may be trained with the annotated information on the medical device group. In an example, the medical device group may include a plurality of medical devices capable of determining the presence or absence of at least a part of the medical device based on the same marker and/or the same normal area.

According to an embodiment, the processor may acquire a plurality of reference medical images that include one or more reference medical devices, and acquire annotations for reference groups associated with one or more reference medical devices included in the plurality of reference medical images. In this case, the second machine learning model 600 may be trained to receive the plurality of reference medical images, and extract reference groups associated with the one or more reference medical devices in the plurality of reference medical images based on the annotations for the reference groups associated with the one or more reference medical devices. For example, the annotation may be performed by image-level labeling, pixel-level labeling, and the like, and may include segmentation annotation. Then, the processor may input the information on the group of reference medical devices annotated as described above to the second machine learning model 600 to train the second machine learning model 600.

In FIGS. 5 and 6, the first machine learning model 500 and the second machine learning model 600 have been described above as being separated from each other, but embodiments are not limited thereto. For example, the first machine learning model 500 and the second machine learning model 600 may be implemented as one machine learning model or two or more machine learning models. In another example, the second machine learning model 600 may be implemented as a plurality of different machine learning models generated to extract a plurality of medical device groups.

Figure 7:
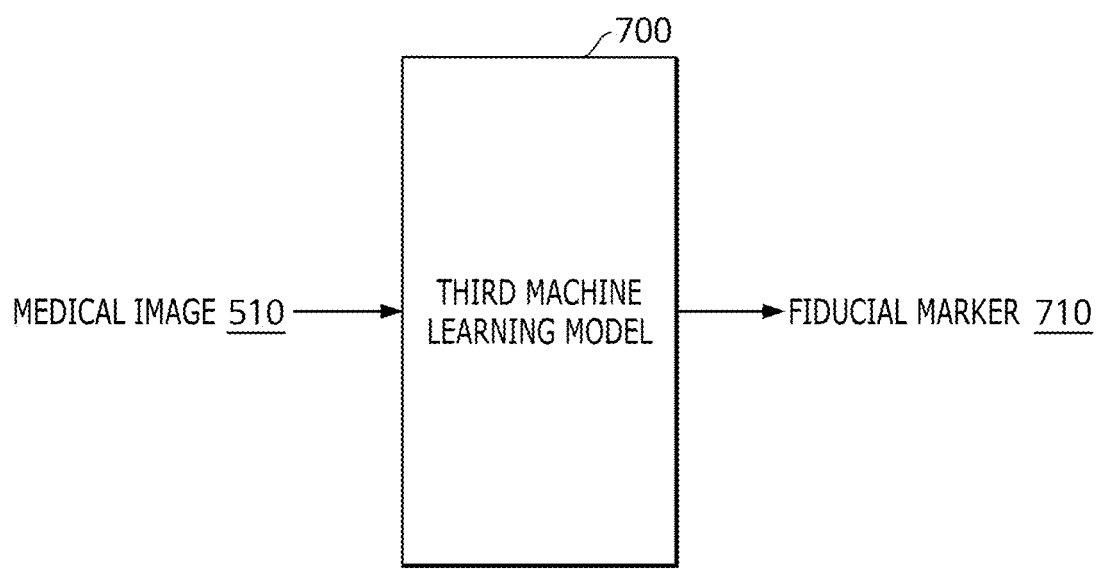
FIG. 7 is a diagram illustrating an example of a third machine learning model according to an embodiment of the present disclosure.

FIG. 7 illustrates an example of a third machine learning model 700 according to an embodiment of the present disclosure. As illustrated, the third machine learning model 700 may receive the medical image 510 and extract a fiducial marker 710 associated with a target medical device from the medical image 510. For example, the third machine learning model 700 may be accessed by or included in the normal area predictor (330 in FIG. 3) described above.

According to an embodiment, the third machine learning model 700 may be trained to output the fiducial marker associated with the target medical device from the medical image. For example, the processor may acquire a plurality of reference medical images that include one or more reference medical devices, and acquire annotations for the reference fiducial markers associated with one or more reference medical devices included in the plurality of reference medical images. In this case, the third machine learning model 700 may be trained to receive the plurality of reference medical images, and extract reference fiducial markers associated with the one or more reference medical devices in the plurality of reference medical images based on the annotations for the reference fiducial markers associated with the one or more reference medical devices. For example, the annotation may be performed by image-level labeling, pixel-level labeling, and the like, and may include segmentation annotation.

Additionally or alternatively, the processor may generate training data for training the third machine learning model 700 by using a reference medical image that does not include the medical device. As described above, the processor may determine or acquire, in the reference medical image, a reference medical device for generating training data and a normal area associated with the reference medical device. Then, the processor may display at least a part of the medical device in the determined normal area in the reference medical image to generate a first set of training data in which the reference medical device is normally positioned, and display at least a part of the reference medical device in an area other than the determined normal area in the reference medical image to generate a second set of training data in which the reference medical device is abnormally positioned. In this case, the third machine learning model 700 may be trained with the generated first set of training data and second set of training data.

In FIGS. 5 to 7, the first machine learning model 500, the second machine learning model 600, and the third machine learning model 700 have been described above as being separated from each other, but embodiments are not limited thereto. According to an embodiment, the first machine learning model 500, the second machine learning model 600, and the third machine learning model 700 may be implemented as one machine learning model or implemented as two or more machine learning models. For example, one machine learning model may be configured to extract or detect, through MTL (Multi-Task Learning) or the like, the information on the position of at least a part of the target medical device, whether or not the target medical device is included, the fiducial markers, and the like. In another example, the third machine learning model 700 may be implemented as a plurality of machine learning models configured to detect the presence or absence of an abnormality in a plurality of target medical devices.

Figure 8:
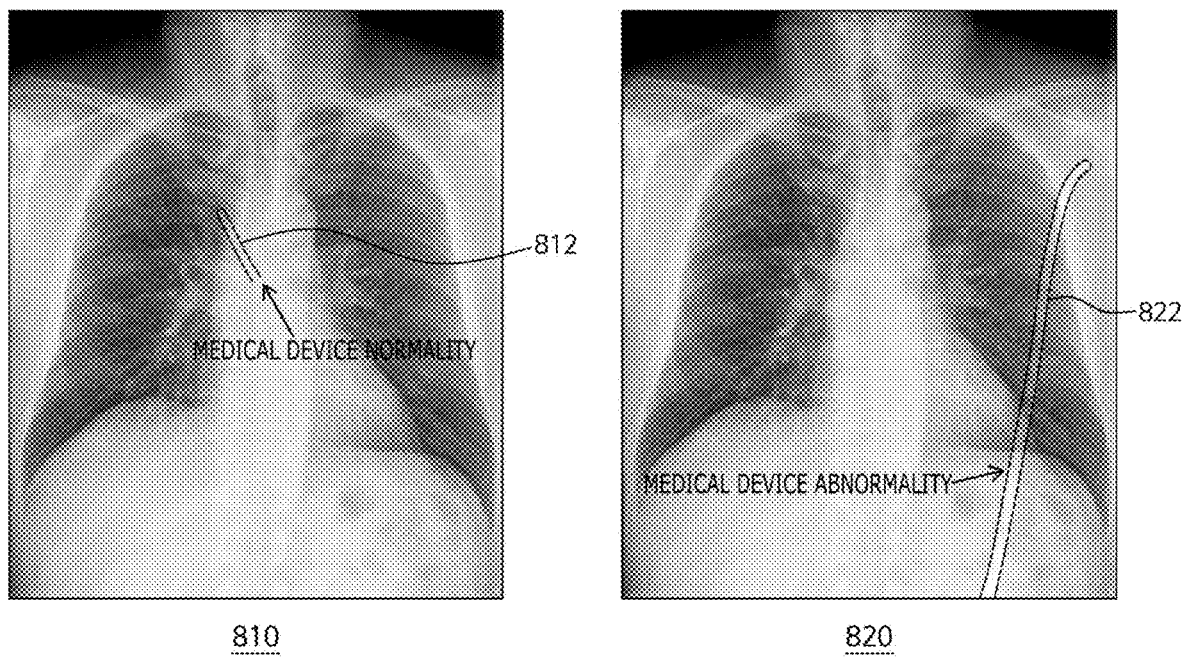
FIG. 8 is a diagram illustrating example display of a medical device on a medical image according to an embodiment of the present disclosure.

FIG. 8 is a diagram illustrating an example in which medical devices 812 and 822 are displayed on medical images 810 and 820 according to an embodiment of the present disclosure. As described above, the processor (e.g., 220 of FIG. 2) may detect the information on the target medical devices 812 and 822 from the medical images 810 and 820. For example, the information on the target medical devices 812 and 822 may include any information for determining the presence or absence of an abnormality in the medical device.

According to an embodiment, the medical image 810 may represent an image in which the target medical device 812 is normally positioned. For example, if the target medical device 812 is normally positioned, a text ("medical device normality"), guide lines, and the like indicating that the target medical device 812 is normal, may be included in the medical image 810. In addition, the medical image 820 may represent an image in which the target medical device 822 is not normally positioned. For example, if there is an abnormality in the target medical device 822, a text ("medical device abnormality"), guide lines, and the like indicating that there is an abnormality in the target medical device 822 may be included in the medical image 820.

According to an embodiment, if receiving the medical images 810 and 820, the processor may input the received medical images 810 and 820 into one machine learning model to determine the presence or absence of an abnormality in the target medical devices 812 and 822. For example, the one machine learning model may be a model trained to determine an abnormality in a medical device from a medical image. Additionally or alternatively, the processor may input the received medical images 810 and 820 into a plurality of machine learning models to determine the presence or absence of an abnormality in the target medical devices 812 and 822. For example, the plurality of machine learning models may be models trained to detect or extract information on the position of at least a part of the target medical device, whether or not the target medical device is included, the fiducial marker, and the like from the medical image.

Figure 9:
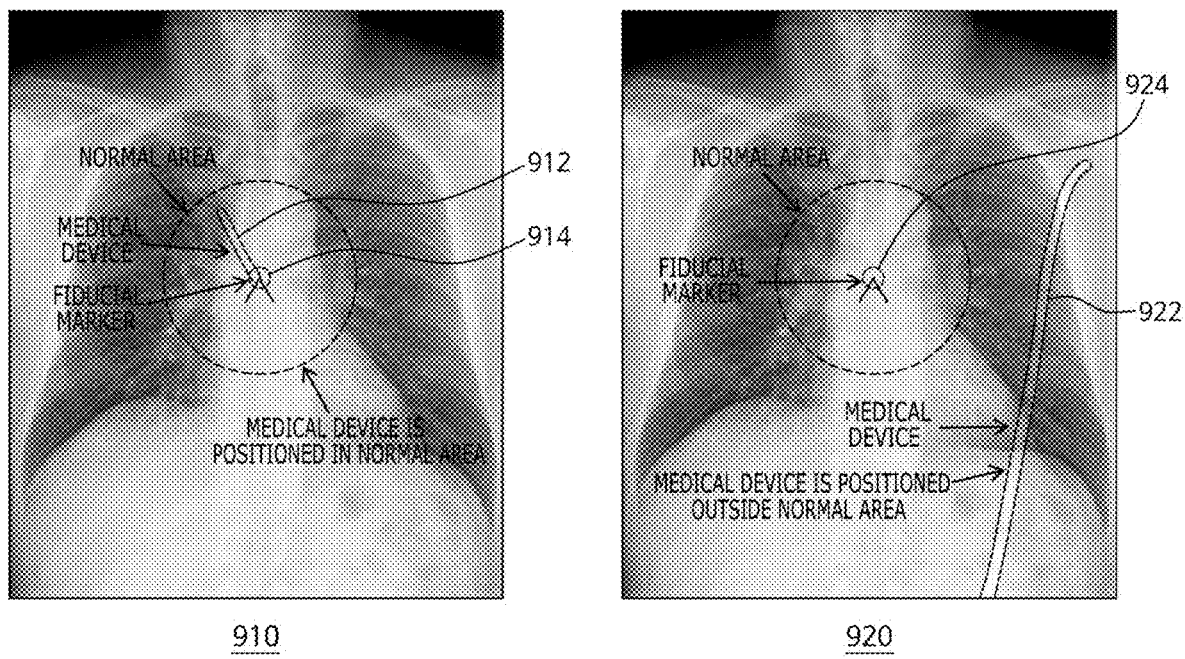
FIG. 9 is a diagram illustrating example display of a medical device on a medical image displayed with reference to a fiducial marker according to an embodiment of the present disclosure.

FIG. 9 is a diagram illustrating an example in which medical devices 912 and 922 are displayed on medical images 910 and 920 with reference to fiducial markers 914 and 924 according to an embodiment of the present disclosure. As described above, the processor (220 of FIG. 2) may detect information on the target medical devices 912 and 922 from the medical images 910 and 920. For example, the information on the target medical devices 912 and 922 may be any information for determining the presence or absence of an abnormality in the medical device, and may include information on the fiducial markers 914 and 924 (e.g., carina) and the like.

According to an embodiment, the medical image 910 may represent an image in which the target medical device 912 is normally positioned. For example, if the medical device 912 is positioned within a predetermined distance from the fiducial marker 914, it may be determined to be positioned in the normal area. As illustrated, the processor may extract or determine an area corresponding to the target medical device 912, an area corresponding to the fiducial marker 914, a normal area determined from the fiducial marker 914, and text indicating the presence or absence of an abnormality in the target medical device ("the medical device positioned in the normal area"), and the like, and display the same on the medical image 910. In this case, the processor may display the area described above and the like on the medical image 910 using text, image, guide line, indicator, or the like.

According to an embodiment, the medical image 920 may represent an image in which the target medical device 922 is not normally positioned. For example, if the medical device 922 is not positioned within a predetermined distance from the fiducial marker 924, it may be determined to have an abnormality. As illustrated, the processor may extract or determine an area corresponding to the target medical device 922, an area corresponding to the fiducial marker 924, a normal area determined from the fiducial marker 924, and text indicating the presence or absence of an abnormality in the target medical device ("the medical device positioned outside the normal area"), and the like, and display the same on the medical image 920.

Figure 10:
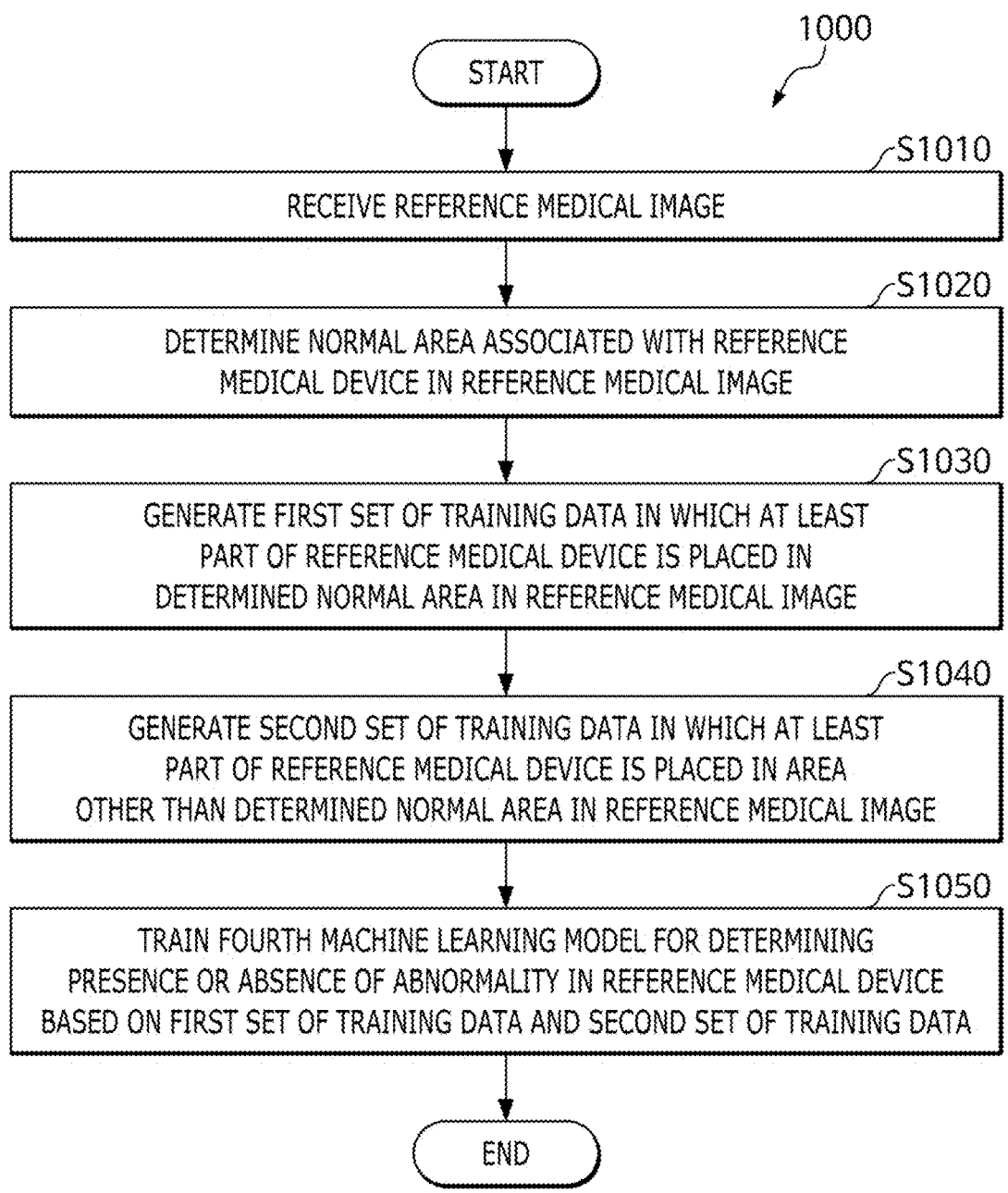
FIG. 10 is a flowchart illustrating a training method for determining an abnormality in a medical device according to an embodiment of the present disclosure.

FIG. 10 is a flowchart illustrating a training method 1000 for determining an abnormality in a medical device according to an embodiment of the present disclosure. According to an embodiment, the training method 1000 for determining an abnormality in a medical device may be performed by a processor (e.g., a processor of a user terminal and/or at least one processor of an information processing system). As illustrated, in the method 1000 for determining an abnormality in the medical device, the processor may receive a reference medical image (S1010). For example, the processor may receive a reference medical image that does not include a medical device, which may be taken directly by any device associated with the information processing system, or may receive a reference medical image from an external device (e.g., a user terminal or a database).

The processor may determine a normal area associated with the reference medical device in the reference medical image (S1020). According to an embodiment, the processor may receive information on the normal area associated with the position of at least a part of the reference medical device from the external device, and apply the normal area associated with the position of the at least the part associated with the reference medical device to the reference medical image. Additionally or alternatively, the processor may receive information on a reference medical device for generating training data from an external device, and extract the normal area associated with the reference medical device in the reference medical image based on the received information on the reference medical device and the information on the reference medical image.

The processor may generate a first set of training data in which at least a part of the reference medical device is placed in the determined normal area in the reference medical image (S1030). For example, at least a part of the reference medical device may be displayed in the determined normal area in the reference medical image, and as a result, the first set of training data may include the training data, that is, the normal training data in which the reference medical device is normally positioned. In addition, the processor may generate a second set of training data in which at least a part of the reference medical device is placed in an area other than the determined normal area in the reference medical image (S1040). For example, at least a part of the reference medical device may be displayed in an area other than the determined normal area in the reference medical image, and as a result, the second set of training data may include the training data, that is, the abnormal training data in which the reference medical device is abnormally positioned. Then, the processor may train a fourth machine learning model for determining the presence or absence of an abnormality in the reference medical device based on the first set of training data and the second set of training data (S1050). For example, the processor may receive the medical image, detect the information on at least a part of the target medical device included in the received medical image, and use the trained machine learning model to determine the presence or absence of an abnormality in the target medical device based on whether or not the target medical device is placed in the normal area.

According to an embodiment, the fourth machine learning model may include a binary classification model that is trained to classify the reference medical image into normal data or abnormal data. For example, the binary classification model may be trained to output "1" (normal data) in response to the input of the first set of training data in which the reference medical device is normally positioned, and output "0" (abnormal data) in response to the input of the second set of training data in which the reference medical device is abnormally positioned.

Figure 11:
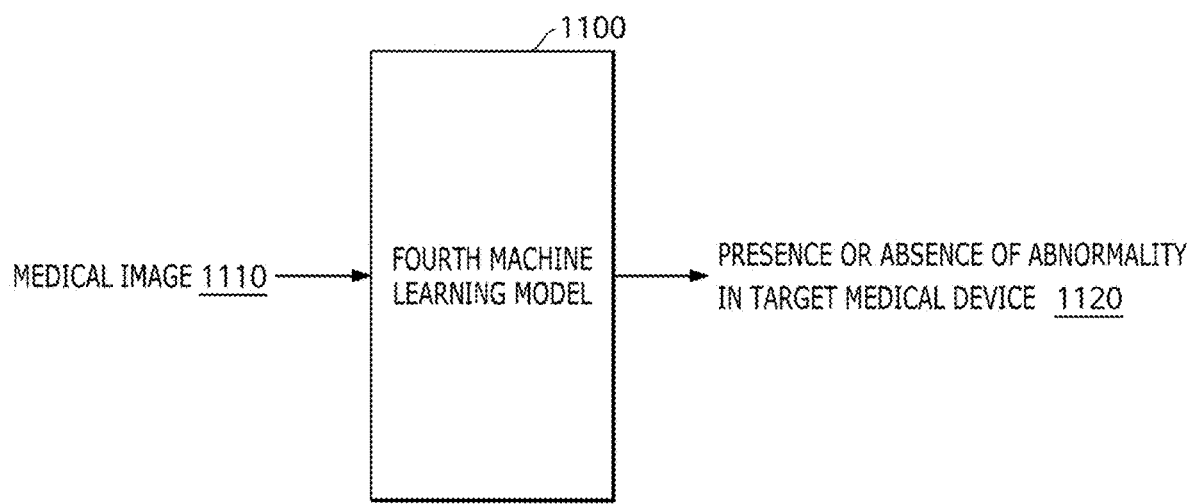
FIG. 11 is a diagram illustrating an example of a fourth machine learning model according to an embodiment of the present disclosure.

FIG. 11 illustrates an example of a fourth machine learning model 1100 according to an embodiment of the present disclosure. As illustrated, the fourth machine learning model 1100 may receive a medical image 1110 and determine the presence or absence of an abnormality in a target medical device 1120.

According to an embodiment, the processor (220 of FIG. 2) may receive a reference medical image and determine a normal area associated with the reference medical device in the reference medical image. Then, the processor may display at least a part of the reference medical device in the determined normal area in the reference medical image to generate a first set of training data in which the reference medical device is normally positioned. In addition, the processor may display at least a part of the reference medical device in an area other than the determined normal area in the reference medical image to generate a second set of training data in which the reference medical device is abnormally positioned. Furthermore, the processor may train a fourth machine learning model for determining the presence or absence of an abnormality in the reference medical device based on the first set of training data and the second set of training data. In an example, the fourth machine learning model may include a binary classification model that is trained to classify the reference medical image into normal data or abnormal data.

Additionally or alternatively, the processor may receive the reference medical image, display at least a part of the reference medical device in the reference medical image to generate third training data in which the medical device is normal, and display at least a part of damaged reference medical device in the reference medical image to generate fourth training data in which the medical device is abnormal. Then, the processor may train a fourth machine learning model for determining the presence or absence of an abnormality in the reference medical device based on the third set of training data and the fourth set of training data.

According to an embodiment, the processor may receive a medical image and detect information on at least a part of a target medical device included in the received medical image. Then, the processor may use the trained fourth machine learning model to determine the presence or absence of an abnormality in the target medical device based on whether or not the target medical device is placed in the normal area. Additionally or alternatively, the processor may use the trained fourth machine learning model to determine the presence or absence of an abnormality in the target medical device based on the presence or absence of damage in the target medical device. In an example, if the fourth machine learning model is a binary classification model, the medical image may be classified into normal data or abnormal data through the fourth machine learning model. To this end, the fourth machine learning model may be configured to output information (e.g., "1" or "0") indicating that the medical image is normal data or abnormal data, in response to the input of the medical image.

Figure 12:
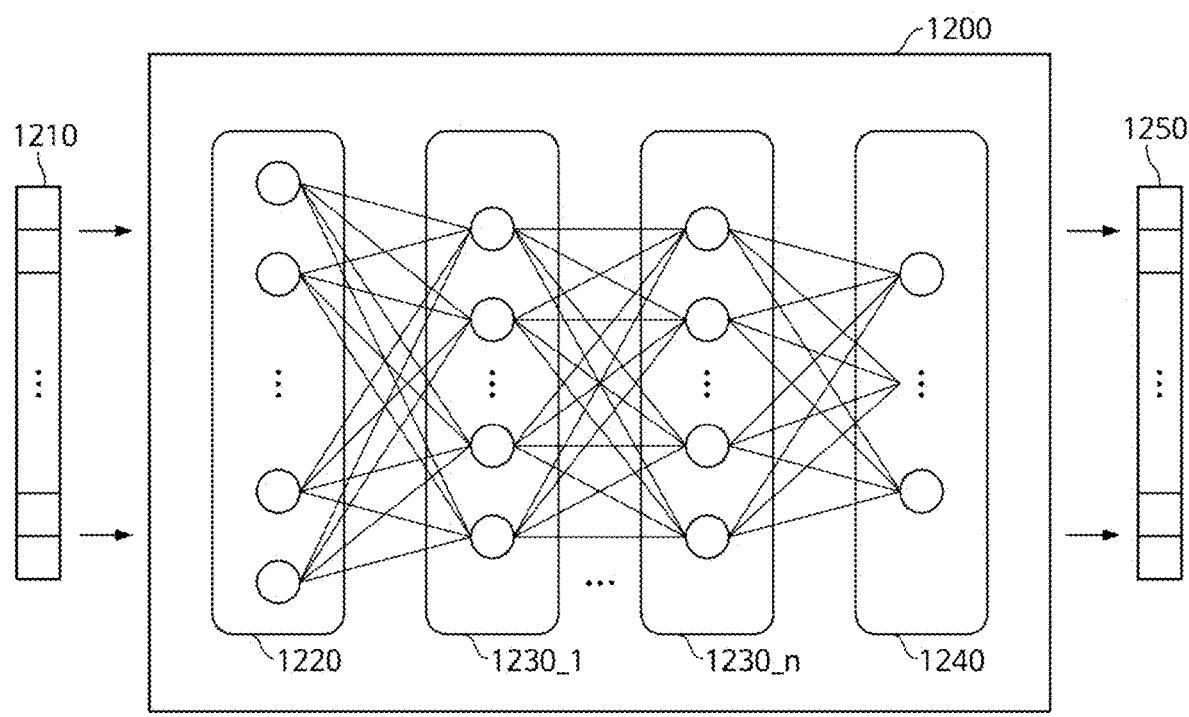
FIG. 12 is an exemplary diagram illustrating an artificial neural network model according to an embodiment of the present disclosure.

FIG. 12 is an exemplary diagram illustrating an artificial neural network model 1200 according to an embodiment of the present disclosure. In machine learning technology and cognitive science, the artificial neural network model 1200 as an example of the machine learning model refers to a statistical learning algorithm implemented based on a structure of a biological neural network, or to a structure that executes such algorithm.

According to an embodiment, the artificial neural network model 1200 may represent a machine learning model having a problem solving ability by repeatedly adjusting the weights of synapses by the nodes that are artificial neurons forming the network through synaptic combinations as in the biological neural networks, thus training to reduce errors between a target output corresponding to a specific input and a deduced output. For example, the artificial neural network model 1200 may include any probability model, neural network model, and the like, that is used in artificial intelligence training methods such as machine learning and deep learning.

According to an embodiment, the first to fourth machine learning models described above may be generated in the form of the artificial neural network model 1200. For example, the artificial neural network model 1200 may receive a medical image and output information on at least a part of a target medical device included in the medical image. In another example, the artificial neural network model 1200 may detect information on a fiducial marker, a normal area, and the like associated with the target medical device included in the medical image. As another example, the artificial neural network model 1200 may extract the normal area associated with the target medical device from the medical image. In still another example, the artificial neural network model 1200 may detect, from the received medical image, whether or not the target medical device is included.

The artificial neural network model 1200 is implemented as a multilayer perceptron (MLP) formed of multiple nodes and connections between them. The artificial neural network model 1200 according to an embodiment may be implemented using one of various artificial neural network model structures including the MLP. As illustrated in FIG. 12, the artificial neural network model 1200 includes an input layer 1220 to receive an input signal or data 1210 from the outside, an output layer 1240 to output an output signal or data 1250 corresponding to the input data, and (n) number of hidden layers 1230_1 to 1230_$n$ (where n is a positive integer) positioned between the input layer 1220 and the output layer 1240 to receive a signal from the input layer 1220, extract the features, and transmit the features to the output layer 1240. In an example, the output layer 1240 receives signals from the hidden layers 1230_1 to 1230_$n$ and outputs them to the outside.

The method of training the artificial neural network model 1200 includes the supervised learning that trains to optimize for solving a problem with inputs of teacher signals (correct answers), and the unsupervised learning that does not require a teacher signal. The information processing system may train, by supervised and/or unsupervised learning, the artificial neural network model 1200 to determine whether or not at least a part of one or more medical devices included in the medical image is positioned on one or more normal areas. The artificial neural network model 1200 trained as described above may be stored in a memory (not illustrated) of the information processing system, and may determine whether or not at least a part of the target medical device included in the medical image received from the communication module and/or the memory is positioned on the normal area, the presence or absence of damage in at least a part of the target medical device, and the like.

According to an embodiment, the information processing system may directly generate the training data for training the artificial neural network model 1200 through simulation. For example, the information processing system may receive a reference medical image. In addition, the information processing system may determine a normal area associated with a reference medical device in the reference medical image, and display at least a part of the reference medical device in the determined normal area in the reference medical image to generate a first set of training data in which the reference medical device is normally positioned. In addition, the information processing system may display at least a part of the reference medical device in an area other than the determined normal area in the reference medical image to generate a second set of training data in which the reference medical device is abnormally positioned. Then, the information processing system may train the artificial neural network model 1200 for determining the presence or absence of an abnormality in the reference medical device based on the first set of training data and the second set of training data.

According to an embodiment, the input variable of the artificial neural network model 1200 may include a medical image associated with a medical device or any information indicating the medical image. Additionally or alternatively, the input variable of the artificial neural network model 1200 may include a first set of training data in which the medical device is normally positioned, a second set of training data in which the medical device is abnormally positioned, and the like. In addition, when the artificial neural network model 1200 is trained, information on the position of at least a part of the annotated target medical device, information on a fiducial marker and/or a normal area associated with the annotated target medical device, and the like may be used as ground truth.

As described above, if the input variable described above is input through the input layer 1220, the output variable output from the output layer 1240 of the artificial neural network model 1200 may be a vector indicating or characterizing the information on the position of at least a part of the medical device, the information on whether or not the target medical device is included, the fiducial marker associated with the medical device, and/or the presence or absence of an abnormality in the target medical. Additionally or alternatively, the output variable output from the output layer 1240 of the artificial neural network model 1200 may be a vector indicating or characterizing the information on the presence or absence of damage in at least a part of the target medical device included in the medical image.

As described above, the input layer 1220 and the output layer 1240 of the artificial neural network model 1200 are respectively matched with a plurality of output variables corresponding to a plurality of input variables, and as the synaptic values between nodes included in the input layer 1220, and the hidden layers 1230_1 to 1230_n, and the output layer 1240 are adjusted, training can be processed to extract a correct output corresponding to a specific input. Through this training process, the features hidden in the input variables of the artificial neural network model 1200 can be confirmed, and the synaptic values (or weights) between the nodes of the artificial neural network model 1200 can be adjusted so that there can be a reduced error between the target output and the output variable calculated based on the input variable. By using the artificial neural network model 1200 trained as described above, the information on at least a part of the target medical device included in the received medical image may be output.

Figure 13:
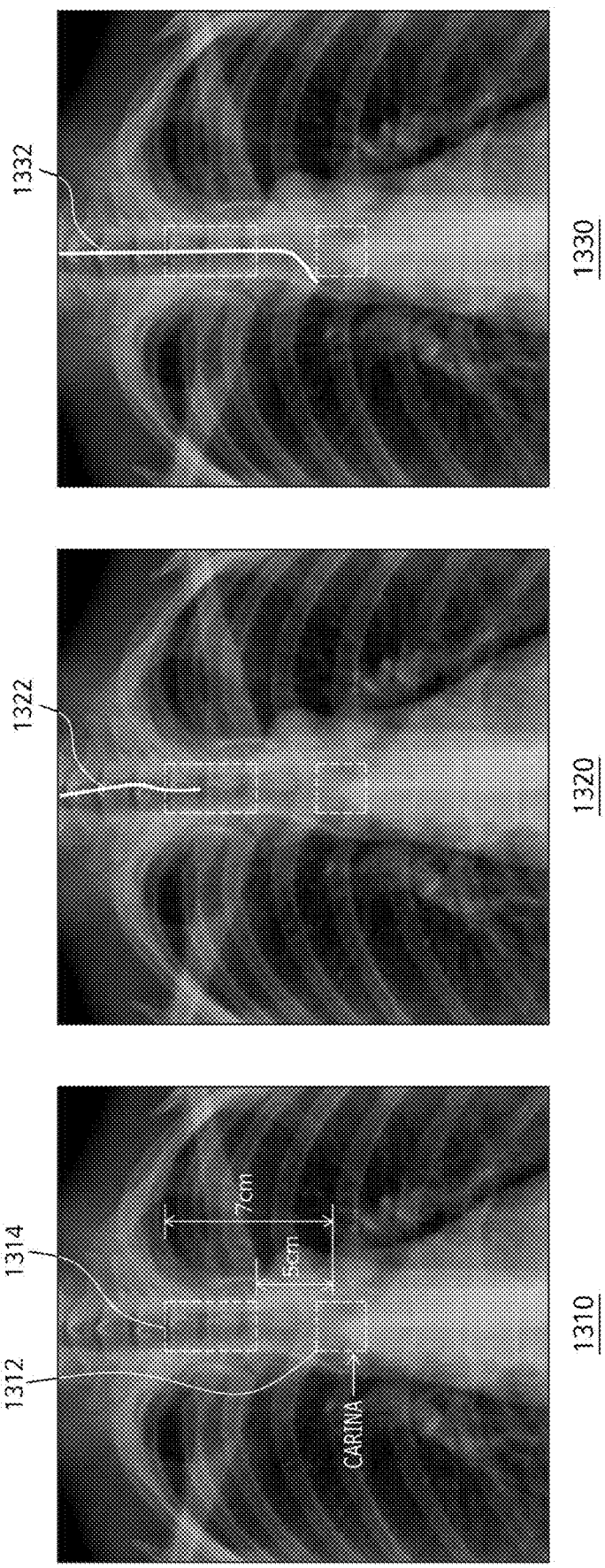
FIG. 13 is a diagram illustrating an example of generating training data according to an embodiment of the present disclosure.

FIG. 13 is a diagram illustrating an example of generating training data according to an embodiment of the present disclosure. According to an embodiment, the processor (220 of FIG. 2) may use a reference medical image 1310 that does not include the medical device, to generate training data for determining an abnormality in the medical device. For example, the processor may display any reference medical device at a specific position in the reference medical image 1310 to generate a medical image 1320 in which a medical device is normal and/or a medical image 1330 in which a medical device has an abnormality.

According to an embodiment, the processor may receive the reference medical image 1310, and determine a normal area 1314 associated with the reference medical device in the reference medical image 1310. For example, the processor may determine that the medical device for generating the training data is an endotracheal tube. In this case, the processor may extract a fiducial marker 1312 serving as a determination criterion to determine the normal area 1314 of the endotracheal tube. For example, the fiducial marker 1312 for determining the normal area 1314 of the endotracheal tube may be a carina. The processor may then set the area between 5 cm and 7 cm above the carina as the normal area 1314 of the endotracheal tube.

According to an embodiment, the processor may display, through simulation, at least a part of the reference medical device 1322 in the determined normal area 1314 in the reference medical image 1310, to thus generate a first set of training data in which the reference medical device 1322 is normally positioned. In the illustrated example, the processor may display the tube tip of the endotracheal tube positioned in the normal area 1314, to thus generate training data in which the reference medical device 1322 is normally positioned. FIG. 13 illustrates that the reference medical device 1322 is displayed to generate one training data, but embodiments are not limited thereto, and the reference medical device 1322 may be displayed such that the tube tip is positioned in the normal area 1314, to generate a plurality of training data.

According to an embodiment, the processor may display, through simulation, at least a part of a reference medical device 1332 in an area other than the normal area determined in the reference medical image 1310, to thus generate a second set of training data in which the reference medical device 1332 is abnormally positioned. In the illustrated example, the processor may display the tube tip of the endotracheal tube positioned in an area other than the normal area 1314, to thus generate training data in which the reference medical device 1332 is abnormally positioned. FIG. 13 illustrates that the reference medical device 1332 is displayed to generate one training data, but embodiments are not limited thereto, and the reference medical device 1332 may be displayed with a part (e.g., the tube tip) of the reference medical device 1332 positioned or not positioned in the normal area 1314 to generate a plurality of training data.

Then, the processor may train at least one machine learning model for determining the presence or absence of an abnormality in the reference medical device based on the generated first set of training data and second set of training data. With such a configuration, even when it is difficult to collect a large amount of medical images in which the medical device normally or abnormally displayed, the processor can effectively generate the training data for training the artificial neural network model only with the medical images.

Figure 14:
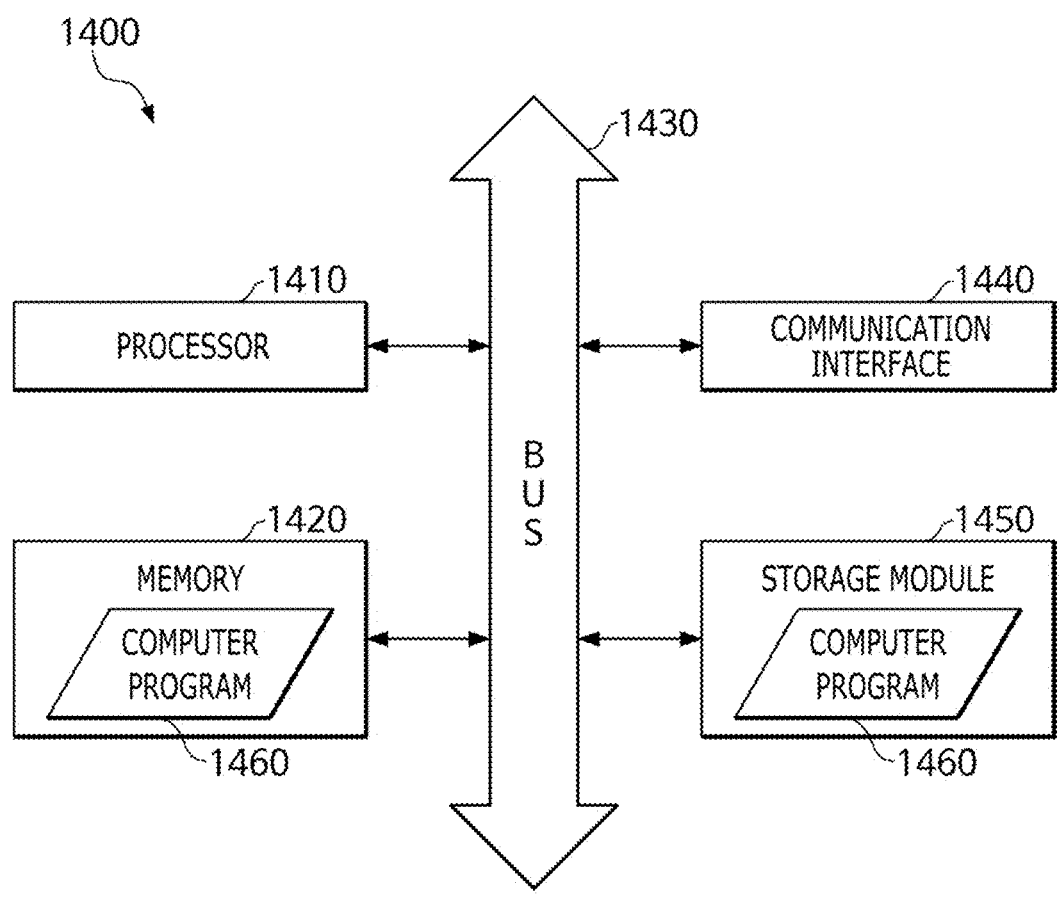
FIG. 14 is a block diagram of any computing device associated with the determination of an abnormality of a medical device according to an embodiment of the present disclosure.

FIG. 14 is a block diagram of any computing device 1400 associated with determining an abnormality of the medical device according to an embodiment of the present disclosure. For example, the computing device 1400 may include the information processing system 120 and/or the user terminal 130. As illustrated, the computing device 1400 may include one or more processors 1410, a bus 1430, a communication interface 1440, a memory 1420 for loading a computer program 1460 to be executed by the processors 1410, and a storage module 1450 for storing the computer program 1460. Meanwhile, only the components related to the embodiment are illustrated in FIG. 14. Accordingly, those of ordinary skill in the art to which the present disclosure pertains will be able to recognize that other general-purpose components may be further included in addition to the components illustrated in FIG. 14.

The processors 1410 control the overall operation of each component of the computing device 1400. The processors 1410 may be configured to include a central processing unit (CPU), a micro processor unit (MPU), a micro controller unit (MCU), a graphic processing unit (GPU), or any type of processor well known in the technical field of the present disclosure. In addition, the processors 1410 may perform an arithmetic operation on at least one application or program for executing the method according to the embodiments of the present disclosure. The computing device 1400 may include one or more processors.

The memory 1420 may store various types of data, commands, and/or information. The memory 1420 may load one or more computer programs 1460 from the storage module 1450 in order to execute the method/operation according to various embodiments of the present disclosure. The memory 1420 may be implemented as a volatile memory such as RAM, but the technical scope of the present disclosure is not limited thereto.

The bus 1430 may provide a communication function between components of the computing device 1400. The bus 1430 may be implemented as various types of buses such as an address bus, a data bus, a control bus, or the like.

The communication interface 1440 may support wired/wireless Internet communication of the computing device 1400. In addition, the communication interface 1440 may support various other communication methods in addition to the Internet communication. To this end, the communication interface 1440 may include a communication module well known in the technical field of the present disclosure.

The storage module 1450 may non-temporarily store one or more computer programs 1460. The storage module 1450 may be configured to include a nonvolatile memory such as a read only memory (ROM), an erasable programmable ROM (EPROM), an electrically erasable programmable ROM (EEPROM), a flash memory, and the like, a hard disk, a detachable disk, or any type of computer-readable recording medium well known in the art to which the present disclosure pertains.

The computer program 1460 may include one or more instructions that, if loaded into the memory 1420, cause the processors 1410 to perform an operation/method in accordance with various embodiments of the present disclosure. That is, the processors 1410 may perform operations/methods according to various embodiments of the present disclosure by executing one or more instructions.

For example, the computer program 1460 may include instructions for receiving a medical image and detecting information on at least a part of a target medical device included in the received medical image. In addition, the computer program 1460 may include instructions for receiving a reference medical image, determining a normal area associated with a reference medical device in the reference medical image, displaying at least a part of the reference medical device in the normal area determined in the reference medical image to generate a first set of training data in which the reference medical device is normally positioned, generating at least a part of the reference medical device in an area other than the determined normal area in the reference medical image to generate a second set of training data in which the reference medical device is abnormally positioned, and training a machine learning model for determining the presence or absence of an abnormality in the reference medical device based on the first set of training data and the second set of training data.

The above description of the present disclosure is provided to enable those skilled in the art to make or use the present disclosure. Various modifications of the present disclosure will be readily apparent to those skilled in the art, and the general principles defined herein may be applied to various modifications without departing from the spirit or scope of the present disclosure. Thus, the present disclosure is not intended to be limited to the examples described herein but is intended to be accorded the broadest scope consistent with the principles and novel features disclosed herein.

Although example implementations may refer to utilizing aspects of the presently disclosed subject matter in the context of one or more standalone computer systems, the subject matter is not so limited, and they may be implemented in conjunction with any computing environment, such as a network or distributed computing environment. Furthermore, aspects of the presently disclosed subject matter may be implemented in or across a plurality of processing chips or devices, and storage may be similarly influenced across a plurality of devices. Such devices may include PCs, network servers, and handheld devices.

Although the present disclosure has been described in connection with certain embodiments herein, it should be understood that various modifications and changes can be made without departing from the scope of the present disclosure, which can be understood by those skilled in the art to which the present disclosure pertains. Further, such modifications and changes are intended to fall within the scope of the claims appended herein.

What is claimed is:

1. A method for determining an abnormality in a medical device in a medical image, the method being executed by at least one processor and comprising:
   receiving a medical image;
   detecting information on at least a part of a target medical device in the received medical image by:
      extracting, from the received medical image, a fiducial marker associated with the target medical device; and
      determining a normal area of the target medical device based on the extracted fiducial marker wherein the normal area is indicative of a region where the medical device is properly located; and
   controlling a display to display information on a position of the at least the part of the target medical device and the normal area of the target medical device on the received medical image,
   wherein the normal area is displayed on the received medical image in at least one form of a mask, region, contour, line or point.

2. The method according to claim 1, wherein the detecting comprises detecting the information on the position of the at least the part of the target medical device in the received medical image by using a first machine learning model.

3. The method according to claim 2, further comprising:
   acquiring a plurality of reference medical images including one or more reference medical devices; and
   acquiring an annotation for a position of at least a part of the one or more reference medical devices included in the plurality of reference medical images, wherein
   the first machine learning model is trained to receive the plurality of reference medical images, and detect information on the one or more reference medical devices included in each of the plurality of reference medical images based on the annotation for the position of the at least the part of the one or more reference medical devices.

4. The method according to claim 2, wherein the detecting the information on the position of the at least the part of the target medical device comprises:
  determining whether or not the target medical device is included in the received medical image by using a second machine learning model; and
  based on the target medical device being in the received medical image, detecting the information on the position of the at least the part of the target medical device in the received medical image by using the first machine learning model.

5. The method according to claim 4, wherein the determining whether or not the target medical device is included in the received medical image by using the second machine learning model comprises determining whether or not a medical device included in the received medical image belongs to the same medical device group as the target medical device, and
  the second machine learning model is trained to receive a plurality of reference medical images and output a medical device group to which a reference medical device included in each of the plurality of reference medical images belongs.

6. The method according to claim 1, wherein the detecting comprises:
  determining presence or absence of an abnormality in the target medical device based on the information on the target medical device and the extracted fiducial marker.

7. The method according to claim 6, wherein the extracting comprises extracting, from the received medical image, the fiducial marker associated with the target medical device by using a third machine learning model.

8. The method according to claim 7, further comprising:
  acquiring a plurality of reference medical images including one or more reference medical devices; and
  acquiring an annotation for a reference fiducial marker associated with the one or more reference medical devices included in the plurality of reference medical images, wherein
  the third machine learning model is trained to receive the plurality of reference medical images, and extract reference fiducial markers associated with the one or more reference medical devices in the plurality of reference medical images based on the annotation for the reference fiducial marker associated with the one or more reference medical devices.

9. The method according to claim 6, wherein the determining the presence or absence of the abnormality in the target medical device comprises
  determining whether or not the at least the part of the target medical device is positioned in the normal area.

10. A non-transitory computer-readable recording medium storing instructions that, when executed by one or more processors, cause performance of the method according to claim 1.

11. A method for determining an abnormality in a medical device in a medical image, the method being executed by at least one processor and comprising:
  receiving a reference medical image;
  determining a normal area associated with a reference medical device in the reference medical image;
  generating a first set of training data in which at least a part of the reference medical device is placed in the determined normal area in the reference medical image;
  generating a second set of training data in which the at least the part of the reference medical device is placed in an area other than the determined normal area in the reference medical image; and
  training a fourth machine learning model for determining presence or absence of an abnormality in the reference medical device based on the first set of training data and the second set of training data.

12. The method according to claim 11, further comprising:
  receiving a medical image; and
  determining the presence or absence of the abnormality in a target medical device included in the medical image by using the fourth machine learning model.

13. The method according to claim 11, wherein the determining comprises:
  receiving, from an external device, information on the normal area associated with a position of the at least the part of the reference medical device; and
  applying the normal area associated with the position of the at least the part associated with the reference medical device to the reference medical image.

14. The method according to claim 11, wherein the determining comprises:
  receiving, from an external device, information on the reference medical device; and
  extracting the normal area associated with the reference medical device in the reference medical image, based on the received information on the reference medical device and the information on the reference medical image.

15. The method according to claim 11, wherein the fourth machine learning model comprises a binary classification model trained to classify the reference medical image into normal data or abnormal data.

16. An information processing system comprising:
  memory storing one or more instructions; and
  at least one processor configured to execute the stored one or more instructions to:
    receive a medical image;
    detect information on at least a part of a target medical device in the received medical image by:
      extracting, from the received medical image, a fiducial marker associated with the target medical device; and
      determining a normal area of the target medical device based on the extracted fiducial marker wherein the normal area is indicative of a region where the medical device is properly located; and
    control a display to display information on a position of the at least the part of the target medical device and the normal area of the target medical device on the received medical image,
  wherein the normal area is displayed on the received medical image in at least one form of a mask, region, contour, line or point.

17. The information processing system according to claim 16, wherein the at least one processor is further configured to detect the information on the position of the at least the part of the target medical device in the received medical image by using a first machine learning model.

18. The information processing system according to claim 17, wherein the at least one processor is further configured to:
  acquire a plurality of reference medical images including one or more reference medical devices; and acquire an annotation for a position of at least a part of the one or more reference medical devices included in the plurality of reference medical images, wherein the first machine learning model is trained to receive the plurality of reference medical images, and detect information on the one or more reference medical devices included in each of the plurality of reference medical images based on the annotation for the position of the at least the part of the one or more reference medical devices.

19. The information processing system according to claim 17, wherein the at least one processor is further configured to determine whether or not the target medical device is included in the received medical image by using a second machine learning model, and based on the target medical device being in the received medical image, detect the information on the position of the at least the part of the target medical device in the received medical image by using the first machine learning model.

20. The information processing system according to claim 16, wherein the at least one processor is further configured to determine presence or absence of an abnormality in the target medical device based on the information on the target medical device and the extracted fiducial marker.

* * * * *